(12) United States Patent
Kanik et al.

(10) Patent No.: US 9,050,342 B2
(45) Date of Patent: Jun. 9, 2015

(54) BENEFICIAL EFFECTS OF COMBINATION THERAPY ON CHOLESTEROL

(75) Inventors: Keith Stuart Kanik, West Hartford, CT (US); Samuel H. Zwillich, East Lyme, CT (US); Mary Gardiner Boy, Mystic, CT (US)

(73) Assignee: Pfizer Inc., New York, NY (US)

( * ) Notice: Subject to any disclaimer, the term of this patent is extended or adjusted under 35 U.S.C. 154(b) by 534 days.

(21) Appl. No.: 13/432,470

(22) Filed: Mar. 28, 2012

(65) Prior Publication Data

US 2012/0252825 A1   Oct. 4, 2012

Related U.S. Application Data

(60) Provisional application No. 61/468,661, filed on Mar. 29, 2011.

(51) Int. Cl.
*A61K 31/519* (2006.01)

(52) U.S. Cl.
CPC .................................. *A61K 31/519* (2013.01)

(58) Field of Classification Search
CPC .................................................... A61K 31/519
USPC ........................................................ 514/265.1
See application file for complete search history.

(56) References Cited

U.S. PATENT DOCUMENTS

| | | |
|---|---|---|
| 4,681,893 A | 7/1987 | Roth |
| 5,273,995 A | 12/1993 | Roth |
| 5,969,156 A | 10/1999 | Briggs et al. |
| 6,121,461 A | 9/2000 | McKenzie |
| 6,627,754 B2 | 9/2003 | Blumenkopf et al. |
| 7,091,208 B2 | 8/2006 | Blumenkopf et al. |
| 2003/0073719 A1 | 4/2003 | Wilcox et al. |

*Primary Examiner* — Raymond Henley, III
(74) *Attorney, Agent, or Firm* — A. David Joran

(57) ABSTRACT

The present invention discloses pharmaceutical combination therapies for the treatment or prevention of diseases in a mammal comprising a Janus Kinase inhibitor or a pharmaceutically acceptable salt thereof and a HMG-CoA reductase inhibitor or a pharmaceutically acceptable salt thereof. Pharmaceutical compositions containing the same and kits for achieving a therapeutic effect in a mammal comprising pharmaceutical combination therapies are further described.

12 Claims, 6 Drawing Sheets

BENEFICIAL EFFECTS OF COMBINATION THERAPY ON CHOLESTEROL

CROSS-REFERENCES TO RELATED APPLICATIONS

This application claims the benefit under 35 U.S.C. §119(e) of U.S. Provisional Patent Application Ser. No. 61/468,661, filed Mar. 29, 2011, which is incorporated herein by reference in its entirety for all purposes.

FIELD OF THE INVENTION

The present invention relates to pharmaceutical combination therapies for the treatment or prevention of diseases related to elevated cholesterol in a mammal, comprising a Janus Kinase (JAK) inhibitor such as inhibitors of the enzyme Janus Kinase 3 (JAK3), including a pyrrolo[2,3-d]pyrimidine compound or a pharmaceutically acceptable salt thereof, and a HMG-CoA reductase inhibitor or a pharmaceutically acceptable salt thereof. The present invention also relates to pharmaceutical compositions comprising the same. The invention further relates to kits for achieving a therapeutic effect in a mammal comprising pharmaceutical combination therapies.

BACKGROUND OF THE INVENTION

JAK3 is a member of the Janus family of protein kinases. Although the other members of this family are expressed by essentially all tissues, JAK3 expression is limited to hematopoietic cells. This is consistent with its essential role in signaling through the receptors for IL-2, IL-4, IL-7, IL-9, IL-15, and IL-21 by non-covalent association of JAK3 with the gamma chain common to these multichain receptors. SCID patient populations have been identified with severely reduced levels of JAK3 protein or with genetic defects to the common gamma chain, suggesting that immunosuppression should result from blocking signaling through the JAK3 pathway. Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases, such as rheumatoid arthritis.

Previous therapeutic methods of using pyrrolo[2,3-d]pyrimidine compounds are mentioned in U.S. Pat. No. 7,091,208, the contents of which are hereby incorporated herein by reference for all purposes. Certain pyrrolo[2,3-d]pyrimidine compounds discussed herein are also discussed in U.S. Pat. No. 6,627,754 and U.S. Publication No. 2003/0073719, the contents of both are hereby incorporated herein by reference for all purposes.

Statins are a family of molecules sharing the capacity to competitively inhibit the hepatic enzyme 3-hydroxy-3-methylglutaryl coenzyme A (HMG-CoA) reductase. This enzyme catalyses the rate-limiting step in the L-mevalonate pathway for cholesterol synthesis. Consequently, statins block cholesterol synthesis and are effective in treating hypercholesterolemia. Moreover, reports of several large clinical trials published during recent years have clearly shown treatment with statins to reduce cardiovascular-related morbidity and mortality in patients with and without coronary disease.

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents.

Atorvastatin calcium, disclosed in U.S. Pat. No. 5,273,995 which is incorporated herein by reference, is currently sold as Lipitor having the chemical name [R—(R*,R*)]-2-(4-fluorophenyl)-8,6-dihydroxy-5-(1-methylethyl)-3-phenyl-4-[(phenylamino)carbonyl]-1H-pyrrole-1-heptanoic acid calcium salt (2:1) trihydrate and the formula

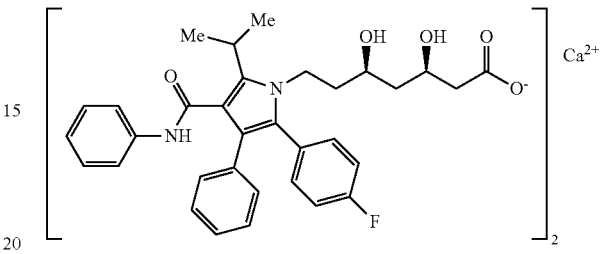

Atorvastatin and pharmaceutically acceptable salts thereof are selective, competitive inhibitors of HMG-CoA reductase. As such, atorvastatin calcium is a potent lipid lowering compound and is thus useful as a hypolipidemic and/or hypocholesterolemic agent.

U.S. Pat. No. 4,681,893, which is incorporated herein by reference, discloses certain trans-6-[2-(3- or 4-carboxamido-substituted-pyrrol-1-yl)alkyl]-4-hydroxy-pyran-2-ones including trans (±)-5-(4-fluorophenyl)-2-(1-methylethyl)-N, 4-diphenyl-1-[(2-tetrahydro-4-hydroxy-6-oxo-2H-pyran-2-yl)ethyl j-1H-pyrrole-3-carboxamide.

U.S. Pat. No. 5,273,995, which is herein incorporated by reference, discloses the enantiomer having the R form of the ring-opened acid of trans-5-(4-fluorophenyl)-2-(l-methylethyl)-N, 4-diphenyl-1-[(2-tetrahydro-4-hydroxy-6-oxo-2H-pyran-2-yl)ethylj-1H-pyrrole-3-carboxamide, ie, [R—(R*R*)]-2-(4-fluorophenyl)-β,δ-dihydroxy-5-(1-methylethyl)-3-phenyl-4-[(phenylamino)-carbonyl-1H-pyrrole-1-heptanoic acid which is atorvastatin.

U.S. Pat. Nos. 5,003,080; 5,097,045; 5,103,024; 5,124,482; 5,149,837; 5,155,251; 5,216,174; 5,245,047; 5,248,793; 5,280,126; 5,397,792; 5,342,952; 5,298,627; 5,446,054; 5,470,981; 5,489,690; 5,489,691; 5,510,488; 5,998,633; and 6,087,511, which are herein incorporated by reference, disclose various processes and key intermediates for preparing atorvastatin.

Crystalline forms of atorvastatin calcium are disclosed in U.S. Pat. Nos. 5,969,156 and 6,121,461, which are incorporated herein by reference.

We have surprisingly and unexpectedly found that those patients who received pharmaceutical combination therapy of JAK3 inhibitors and statins such as atorvastatin showed decreases in LDL level, increases in HDL level, increases in Apolipoprotein A-1, decreases in Apolipoprotein B, decreases in triglycerides level and significant decreases in total cholesterol level.

Because cardiac and inflammation-associated diseases are prevalent throughout the world, the need continues to develop new and improved treatments, as well as agents that will better treat and prevent these diseases. The present invention addresses these and other needs.

SUMMARY OF THE INVENTION

The present invention provides a pharmaceutical combination therapy for the treatment or prevention of a disease related to elevated cholesterol levels in a mammal comprising: a Janus Kinase inhibitor or a pharmaceutically acceptable salt thereof; and a HMG-CoA reductase inhibitor or a pharmaceutically acceptable salt thereof.

In certain embodiments, the Janus Kinase inhibitor is a compound of the formula

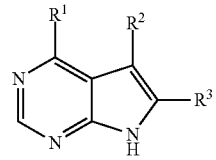

I or the pharmaceutically acceptable salt thereof; wherein $R^1$ is a group of the formula

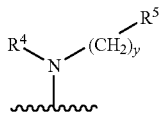

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is $(C_2-C_9)$heterocycloalkyl wherein the heterocycloalkyl groups must be substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino $(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}$N—CO—O—, $R^{15}R^{16}$N—CO—$(C_1-C_6)$alkyl, $(C_1-C_6)$alkyl-S(O)$_m$, $R^{15}R^{16}$NS(O)$_m$, $R^{15}R^{16}$NS(O)$_m$ $(C_1-C_6)$alkyl, $R^{15}$S(O)$_m$$R^{16}$N, $R^{15}$S(O)$_m$$R^{16}$N$(C_1-C_6)$alkyl wherein m is 0, 1 or 2 and $R^{15}$ and $R^{16}$ are each independently selected from hydrogen or $(C_1-C_6)$alkyl; or a group of the formula

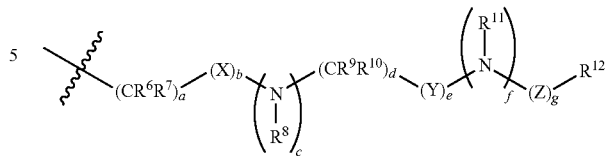

II wherein a is 0, 1, 2, 3 or 4;
b, c, e, f and g are each independently 0 or 1;
d is 0, 1, 2, or 3;
X is S(O)$_n$ wherein n is 0, 1 or 2; oxygen, carbonyl or —C(=N-cyano)-;
Y is S(O)$_n$ wherein n is 0, 1 or 2; or carbonyl; and
Z is carbonyl, C(O)O—, C(O)NR— or S(O)$_n$ wherein n is 0, 1 or 2;
$R^6, R^7, R^8, R^9, R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;
$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$ amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_r$-$C_6)$alkylamino$(C_1-C_6)$acyl, $((C_1-C_6)$alkyl$)_2$amino $(C_1-C_6)$acyl, $R^{15}R^{16}$N—CO—O—, $R^{15}R^{16}$N—CO—$(C_1-C_6)$alkyl, $R^{15}$C(O)NH, $R^{15}$OC(O)NH, $R^{15}$NHC(O)NH, $(C_1-C_6)$alkyl-S(O)$_m$, $(C_1-C_6)$alkyl-S(O)$_m$—$(C_1-C_6)$alkyl, $R^{15}R^{16}$NS(O)$_m$, $R^{15}R^{16}$NS(O)$_m$ $(C_1-C_6)$alkyl, $R^{15}$S(O)$_m$ $R^{16}$N, $R^{15}$S(O)$_m$$R^{16}$N$(C_1-C_6)$alkyl wherein m is 0, 1 or 2 and $R^{15}$ and $R^{16}$ are each independently selected from hydrogen or $(C_1-C_6)$alkyl;
$R^2$ and $R^3$ are each independently selected from the group consisting of hydrogen, deuterium, amino, halo, hydroxy, nitro, carboxy, $(C_2-C_6)$alkenyl, $(C_2-C_6)$alkynyl, trifluoromethyl, trifluoromethoxy, $(C_1-C_6)$alkyl, $(C_1-C_6)$alkoxy, $(C_3-C_{10})$cycloalkyl wherein the alkyl, alkoxy or cycloalkyl groups are optionally substituted by one to three groups selected from halo, hydroxy, carboxy, amino$(C_1-C_6)$alkylthio, $(C_1-C_6)$alkylamino, $((C_1-C_6)$alkyl$)_2$amino, $(C_5-C_9)$heteroaryl, $(C_2-C_9)$heterocycloalkyl, $(C_3-C_9)$cycloalkyl or $(C_6-C_{10})$aryl; or $R^2$ and $R^3$ are each independently $(C_3-C_{10})$cycloalkyl, $(C_3-C_{10})$cycloalkoxy, $(C_1-C_6)$alkylamino, $((C_1-C_6)$alkyl$)_2$amino, $(C_6-C_{10})$arylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfonyl, $(C_6-C_{10})$arylsulfonyl, $(C_1-C_6)$acyl, $(C_1-C_6)$alkoxy-CO—NH—, $(C_1-C_6)$alkyamino-CO—, $(C_5-C_9)$heteroaryl, $(C_2-C_9)$heterocycloalkyl or $(C_6-C_{10})$aryl wherein the heteroaryl, heterocycloalkyl and aryl groups are optionally substituted by one to three halo, $(C_1-C_6)$alkyl, $(C_1-C_6)$alkyl-CO—NH—, $(C_1-C_6)$alkoxy-CO—NH—, $(C_1-C_6)$alkyl-CO—NH—$(C_1-C_6)$alkyl, $(C_r$-$C_6)$alkoxy-CO—NH—$(C_1-C_6)$alkyl, $(C_1-C_6)$alkoxy-CO—NH—$(C_1-C_6)$alkoxy, carboxy, carboxy$(C_1-C_6)$alkyl, carboxy$(C_1-C_6)$alkoxy, benzyloxycarbonyl$(C_1-C_6)$alkoxy, $(C_1-C_6)$alkoxycarbonyl$(C_1-

$C_6$)alkoxy, ($C_6$-$C_{10}$)aryl, amino, amino($C_1$-$C_6$)alkyl, ($C_1$-$C_6$) alkoxycarbonylamino, ($C_6$-$C_{10}$)aryl($C_1$-$C_6$) alkoxycarbonylamino, ($C_1$-$C_6$)alkylamino, (($C_1$-$C_6$)alkyl)$_2$ amino, ($C_1$-$C_6$)alkylamino($C_1$-$C_6$)alkyl, (($C_1$-$C_6$)alkyl)$_2$ amino($C_1$-$C_6$)alkyl, hydroxy, ($C_1$-$C_6$)alkoxy, carboxy, carboxy($C_1$-$C_6$)alkyl, ($C_1$-$C_6$)alkoxycarbonyl, ($C_1$-$C_6$)alkoxycarbonyl($C_1$-$C_6$)alkyl, ($C_1$-$C_6$)alkoxy-CO—NH—, ($C_1$-$C_6$)alkyl-CO—NH—, cyano, ($C_5$-$C_9$)heterocycloalkyl, amino-CO—NH—, ($C_1$-$C_6$)alkylamino-CO—NH—, (($C_1$-$C_6$)alkyl)$_2$amino-CO—NH—, ($C_6$-$C_{10}$)arylamino-CO—NH—, ($C_5$-$C_9$)heteroarylamino-CO—NH—, ($C_1$-$C_6$)alkylamino-CO—NH—($C_1$-$C_6$)alkyl, (($C_1$-$C_6$)alkyl)$_2$amino-CO—NH—($C_1$-$C_6$)alkyl, ($C_6$-$C_{10}$)arylamino-CO—NH—($C_1$-$C_6$)alkyl, ($C_5$-$C_9$)heteroarylamino-CO—NH—($C_1$-$C_6$)alkyl, ($C_1$-$C_6$)alkylsulfonyl, ($C_1$-$C_6$)alkylsulfonylamino, ($C_1$-$C_6$) alkylsulfonylamino($C_1$-$C_6$)alkyl, ($C_6$-$C_{10}$)arylsulfonyl, ($C_6$-$C_{10}$)arylsulfonylamino, ($C_6$-$C_{10}$)arylsulfonylamino($C_1$-$C_6$) alkyl, ($C_1$-$C_6$)alkylsulfonylamino, ($C_1$-$C_6$) alkylsulfonylamino($C_1$-$C_6$)alkyl, ($C_5$-$C_9$)heteroaryl or ($C_2$-$C_9$)heterocycloalkyl.

In another embodiments, the Janus Kinase inhibitor is 3-{(3R,4R)-4-Methyl-3-[methyl-(7H-pyrrolo[2,3-d]-pyrimidin-4-yl)-amino]-piperidin-1-yl}-3-oxopropionitrile or a pharmaceutically acceptable salt thereof.

In certain embodiments, the HMG-CoA reductase inhibitor is a statin.

In other embodiments, the statin is selected from the group consisting of atorvastatin, fluvastatin, lovastatin, pravastatin, simvastatin, cerivastatin, rivastatin, mevastatin, velostatin, compactin, dalvastatin, fluindostatin, rosuvastatin, pitivastatin, and dihydrocompactin.

In some embodiments, the statin is atorvastatin.

In another embodiments, the statin is atorvastatin calcium salt.

In certain embodiments, the mammal is a human.

In certain embodiments, the Janus Kinase inhibitor or a pharmaceutically acceptable salt thereof and the HMG-COA reductase inhibitor or a pharmaceutically acceptable salt thereof are administered simultaneously, sequentially or separately.

In some embodiments, the ratio of Janus Kinase inhibitor or a pharmaceutically acceptable salt thereof to the HMG-CoA reductase inhibitor or a pharmaceutically acceptable salt thereof is about 2:1 to about 1:40 w/w.

In other embodiments, the dosage form is selected from the group consisting of a solution, a suspension, a tablet, a pill, a sachet, a capsule, multiparticulates and a powder.

The present invention also provides a pharmaceutical composition comprising a Janus Kinase inhibitor or a pharmaceutically acceptable salt thereof; and a HMG-CoA reductase inhibitor or a pharmaceutically acceptable salt thereof; and a pharmaceutically acceptable carrier.

The present invention also provides a method of treating a disease related to elevated cholesterol levels in a mammal, comprising administering to a mammal in need thereof a therapeutically effective amount of a Janus Kinase inhibitor and a HMG-CoA reductase inhibitor or a pharmaceutically acceptable salt thereof or a pharmaceutical composition.

In certain embodiments of the invention, the disease treated is selected from the group consisting of atherosclerosis, myocardial infarction, hypocholesterolemia, hyperlipidemia, ischemic heart disease, congestive heart failure, acute coronary syndrome, plaque instability, coronary artery disease, cerebrovascular disease, peripheral vascular disease and cardiac risk management.

The present invention further provides a method of inhibiting cholesterol biosynthesis in a mammal, comprising administering to a mammal in need thereof a Janus Kinase inhibitor and a HMG-CoA reductase inhibitor or a pharmaceutically acceptable salt thereof or a pharmaceutical composition.

The present invention also provides a method of lowering blood cholesterol level in a mammal, comprising administering to a mammal in need thereof a Janus Kinase inhibitor and a HMG-CoA reductase inhibitor or a pharmaceutically acceptable salt thereof or a pharmaceutical composition.

The present invention further provides a kit for achieving a therapeutic effect in a mammal comprising: a therapeutically effective amount of a Janus Kinase inhibitor or a pharmaceutically acceptable salt thereof; and a therapeutically effective amount of a HMG-CoA reductase inhibitor or a pharmaceutically acceptable salt thereof; and a container.

BRIEF DESCRIPTION OF THE DRAWINGS

All the Figures show pharmaceutical combination therapy of tofacitinib (JAK3 inhibitor) and atorvastatin (HMG-CoA reductase inhibitor), or tofacitinib (JAK3 inhibitor) and placebo.

DETAILED DESCRIPTION OF THE INVENTION

Figure 1:
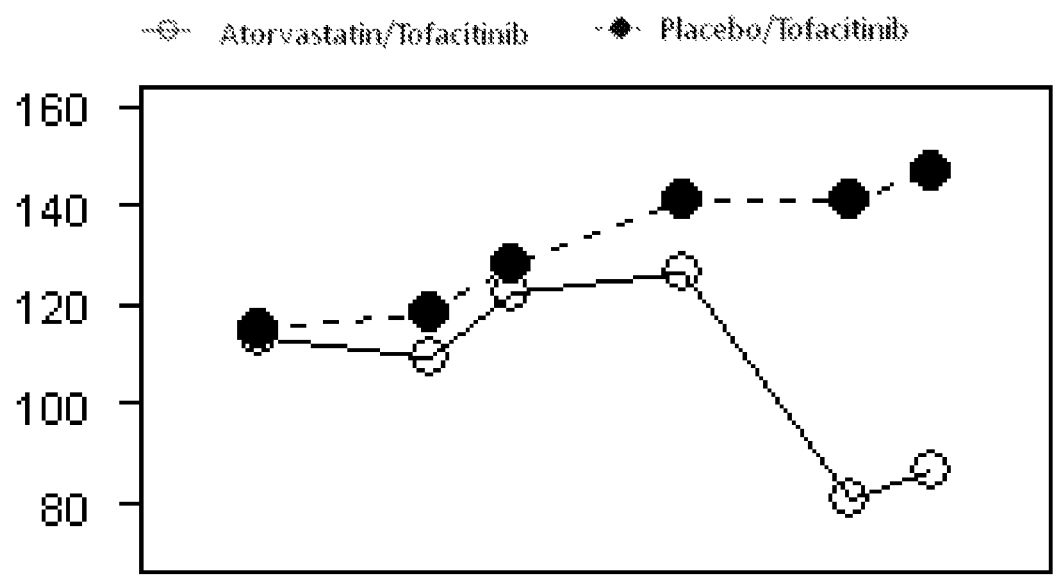
FIG. 1 shows decrease in LDL level after baseline visit for patients who received pharmaceutical combination therapy of tofacitinib and atorvastatin.

Although specific embodiments of the present disclosure will now be described with reference to certain preferred embodiments described in the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs.

DEFINITIONS

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise. Thus, for example, reference to "a compound" includes a plurality of compounds.

The term "alkyl", as used herein, unless otherwise indicated, includes saturated monovalent hydrocarbon radicals having straight or branched moieties or combinations thereof.

The term "alkoxy", as used herein, includes O-alkyl groups wherein "alkyl" is defined above.

The term "halo", as used herein, unless otherwise indicated, includes fluoro, chloro, bromo or iodo.

The term "($C_2$-$C_9$)heterocycloalkyl", as used herein, refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said ($C_2$-$C_9$)heterocycloalkyl rings is through a carbon or a $sp^3$ hybridized nitrogen heteroatom.

The term "($C_2$-$C_9$)heteroaryl", as used herein, refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said ($C_2$-$C_9$)heterocycloalkyl rings is through a carbon atom or a $sp^3$ hybridized nitrogen heteroatom.

($C_6$-$C_{10}$)aryl when used herein refers to phenyl or naphthyl.

The terms "inflammation" and "inflammation-associated" refer to any and all such inflammatory reactions including, but not limited to, immune-related responses and/or allergic reactions to a physical, chemical, or biological stimului. Such inflammation-associated diseases include for example, osteoarthritis, rheumatoid arthritis, osteoarthritic joint pain, rheumatoid arthritic joint, joint pain, inflammatory pain, acute pain, chronic pain, and cartilage damage.

The terms "uses", "utilizes", and "employs", and their derivatives thereof, are used interchangeably when describing an aspect of an invention method, composition, or combination.

The terms "including," "having," and "containing" are open ended unless otherwise indicated.

The term "nontoxic" means the efficacious dose is 10 times or greater than the dose at which a toxic effect is observed in 10% or more of a patient population.

The term "patient" means a mammal, and the two terms are used interchangeably herein.

The term "mammal" includes humans, companion animals such as cats and dogs, livestock animals such as horses, cows, pigs, goats, and sheep, and laboratory animals such as guinea pigs, rabbits, rats, mice, hamsters, and monkeys, and transgenic variants thereof. A human patient is preferred. Also preferred are companion animals, particularly dogs, cats, and horses. Also preferred are laboratory animals, particularly rabbits, rats, mice, and monkeys, and transgenic variants thereof.

The terms "treat" and "treating," as used herein, refer to partially or completely alleviating, inhibiting, ameliorating and/or relieving a condition from which a patient is suspected to suffer.

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "therapeutically effective amount" as used herein, refers to that amount of the therapeutic agent sufficient to result in amelioration of one or more symptoms of a disorder, or prevent advancement of a disorder, or cause regression of the disorder. For example, with respect to the treatment of asthma, a therapeutically effective amount preferably refers to the amount of a therapeutic agent that increases peak air flow by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The term "pharmaceutical combination therapy" or just "combination therapy" as used herein generally refers to the administration of a Janus Kinase inhibitor in combination with a HMG-CoA reductase inhibitor disclosed herein. In other words, the term "pharmaceutical combination therapy" means the Janus Kinase inhibitor, such as a compound of formula (I), may be administered concomitantly in a pharmaceutically acceptable form with a HMG-CoA reductase inhibitor disclosed herein: (i) in the same dosage form, e.g., the same tablet or pharmaceutical composition meaning a pharmaceutical composition comprising a Janus Kinase inhibitor, such as a compound of formula (I), a HMG-CoA reductase inhibitor disclosed herein, and a pharmaceutically acceptable carrier; (ii) in a separate dosage form having the same mode of administration, e.g., a kit comprising a first pharmaceutical composition suitable for oral administration comprising a Janus Kinase inhibitor, such as a compound of formula (I) and a pharmaceutically acceptable carrier, and a second pharmaceutical composition suitable for oral administration comprising a HMG-CoA reductase inhibitor disclosed herein and a pharmaceutically acceptable carrier; and (iii) in a separate dosage form having different modes of administration, e.g., a kit comprising a first pharmaceutical composition suitable for oral administration comprising a Janus Kinase inhibitor, such as a compound of formula (I) and a pharmaceutically acceptable carrier, and a second pharmaceutical composition suitable for parenteral administration comprising a HMG-CoA reductase inhibitor disclosed herein and a pharmaceutically acceptable carrier. Further, those of skill in the art given the benefit of the present disclosure will appreciate that when a HMG-CoA reductase inhibitor disclosed herein is being administered, the agents need not share the same mode of administration, e.g., a kit comprising a first pharmaceutical composition suitable for oral administration comprising a Janus Kinase inhibitor, such as a compound of formula (I) and a pharmaceutically acceptable carrier, a second pharmaceutical composition suitable for oral administration comprising a first a HMG-COA reductase inhibitor disclosed herein and a pharmaceutically acceptable carrier, and a third pharmaceutical composition suitable for parenteral administration comprising a second a HMG-CoA reductase inhibitor disclosed herein and a pharmaceutically acceptable carrier. Those of skill in the art will appreciate that the concomitant administration referred to above in the context of a "pharmaceutical combination therapy" means that the pharmaceutical composition comprising a Janus Kinase inhibitor and a pharmaceutical composition(s) comprising the a HMG-CoA reductase inhibitor can be administered on the same schedule, i.e., at the same time and day, or on a different schedule, i.e., on different, although not necessarily distinct, schedules. In that regard, when the pharmaceutical composition comprising a Janus Kinase inhibitor and a pharmaceutical composition(s) comprising the a HMG-CoA reductase inhibitor is administered on a different schedule, such a different schedule may also be referred to herein as "background" or "background administration." For example, the pharmaceutical composition comprising a Janus Kinase inhibitor may be administered in a certain dosage form twice a day, and the pharmaceutical composition(s) comprising the a HMG-CoA reductase inhibitor may be administered once a day, such that the pharmaceutical composition comprising the Janus Kinase inhibitor may but not necessarily be administered at the same time as the pharmaceutical composition(s) comprising the a HMG-CoA reductase inhibitor during one of the daily administrations. Of course, other suitable variations to "pharmaceutical combination therapy" will be readily apparent to those of skill in the art given the benefit of the present disclosure and are part of the meaning of this term.

The term "Janus Kinase inhibitor" as used herein means a compound(s) that demonstrates an inhibitory effect against one or more Janus Kinases, i.e., one of JAK1, JAK2, and JAK3, as measured by the Biological Assays disclosed herein. Exemplary Janus Kinase inhibitors include those of Formula I disclosed here. A preferable Janus Kinase inhibitor is 3-{(3R,4R)-4-Methyl-3-[methyl-(7H-pyrrolo-[2,3-d]pyrimidin-4-yl)-amino]-piperidin-1-yl}-3-oxo-propionitrile or a pharmaceutically acceptable salt thereof.

The term "co-administering" means the "concomitant" administering of a Janus Kinase inhibitor and a HMG-COA reductase inhibitor, as the term "concomitant" is used in the definition of "pharmaceutical combination therapy".

In one aspect, this disclosure relates to a pharmaceutical combination therapy for the treatment or prevention of rheumatoid arthritis in a human comprising a Janus Kinase inhibitor or a pharmaceutically acceptable salt thereof and a HMG-COA reductase inhibitor or a pharmaceutically acceptable salt thereof.

In certain embodiments, the Janus Kinase inhibitor is a compound of the formula

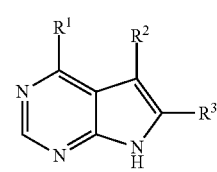

I or a pharmaceutically acceptable salt thereof; wherein
$R^1$ is a group of the formula

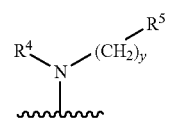

wherein y is 0, 1 or 2;

$R^4$ is selected from the group consisting of hydrogen, ($C_1$-$C_6$)alkyl, ($C_1$-$C_6$)alkylsulfonyl, ($C_2$-$C_6$)alkenyl, ($C_2$-$C_6$)alkynyl wherein the alkyl, alkenyl and alkynyl groups are optionally substituted by deuterium, hydroxy, amino, trifluoromethyl, ($C_1$-$C_4$)alkoxy, ($C_1$-$C_6$)acyloxy, ($C_1$-$C_6$)alkylamino, (($C_1$-$C_6$)alkyl)$_2$amino, cyano, nitro, ($C_2$-$C_6$)alkenyl, ($C_2$-$C_6$)alkynyl or ($C_1$-$C_6$)acylamino; or $R^4$ is ($C_3$-$C_{10}$)cycloalkyl wherein the cycloalkyl group is optionally substituted by deuterium, hydroxy, amino, trifluoromethyl, ($C_1$-$C_6$)acyloxy, ($C_1$-$C_6$)acylamino, ($C_1$-$C_6$)alkylamino, (($C_1$-$C_6$)alkyl)$_2$amino, cyano, cyano($C_1$-$C_6$)alkyl, trifluoromethyl($C_1$-$C_6$)alkyl, nitro, nitro($C_1$-$C_6$)alkyl or ($C_1$-$C_6$)acylamino;

$R^5$ is ($C_2$-$C_9$)heterocycloalkyl wherein the heterocycloalkyl groups must be substituted by one to five carboxy, cyano, amino, deuterium, hydroxy, ($C_1$-$C_6$)alkyl, ($C_1$-$C_6$)alkoxy, halo, ($C_1$-$C_6$)acyl, ($C_1$-$C_6$)alkylamino, amino($C_1$-$C_6$)alkyl, ($C_1$-$C_6$)alkoxy-CO—NH, ($C_1$-$C_6$)alkylamino-CO—, ($C_2$-$C_6$)alkenyl, ($C_2$-$C_6$)alkynyl, ($C_1$-$C_6$)alkylamino, amino($C_1$-$C_6$)alkyl, hydroxy($C_1$-$C_6$)alkyl, ($C_1$-$C_6$)alkoxy($C_1$-$C_6$)alkyl, ($C_1$-$C_6$)acyloxy($C_1$-$C_6$)alkyl, nitro, cyano($C_1$-$C_6$)alkyl, halo($C_1$-$C_6$)alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$)alkoxy($C_1$-$C_6$)acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}$N—CO—O—, $R^{15}R^{16}$N—CO—($C_1$-$C_6$)alkyl, ($C_1$-$C_6$)alkyl-S(O)$_m$, $R^{15}R^{16}$NS(O)$_m$, $R^{15}R^{16}$NS(O)$_m$ ($C_1$-$C_6$)alkyl, $R^{15}$S(O)$_m R^{16}$N, $R^{15}$S(O)$_m R^{16}$N($C_1$-$C_6$)alkyl wherein m is 0, 1 or 2 and $R^{15}$ and $R^{16}$ are each independently selected from hydrogen or ($C_1$-$C_6$)alkyl; or a group of the formula

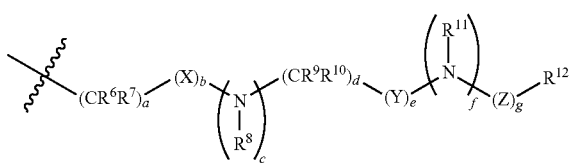

wherein a is 0, 1, 2, 3 or 4;
b, c, e, f and g are each independently 0 or 1;
d is 0, 1, 2, or 3;
X is $S(O)_n$ wherein n is 0, 1 or 2; oxygen, carbonyl or —C(=N-cyano)-;
Y is $S(O)_n$ wherein n is 0, 1 or 2; or carbonyl; and
Z is carbonyl, C(O)O—, C(O)NR— or $S(O)_n$ wherein n is 0, 1 or 2;
$R^6, R^7, R^8, R^9, R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;
$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$ amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}C(O)NH, R^{15}OC(O)NH, R^{15}NHC(O)NH, (C_1-C_6)$alkyl-$S(O)_m$, $(C_1-C_6)$alkyl-$S(O)_m$—$(C_1-C_6)$alkyl, $R^{15}R^{16}NS(O)_m$, $R^{15}R^{16}NS(O)_m$ $(C_1-C_6)$alkyl, $R^{15}S(O)_m$ $R^{16}N, R^{15}S(O)_m R^{16}N(C_1-C_6)$alkyl wherein m is 0, 1 or 2 and $R^{15}$ and $R^{16}$ are each independently selected from hydrogen or $(C_1-C_6)$alkyl;
$R^2$ and $R^3$ are each independently selected from the group consisting of hydrogen, deuterium, amino, halo, hydroxy, nitro, carboxy, $(C_2-C_6)$alkenyl, $(C_2-C_6)$alkynyl, trifluoromethyl, trifluoromethoxy, $(C_1-C_6)$alkyl, $(C_1-C_6)$alkoxy, $(C_3-C_{10})$cycloalkyl wherein the alkyl, alkoxy or cycloalkyl groups are optionally substituted by one to three groups selected from halo, hydroxy, carboxy, amino$(C_1-C_6)$alkylthio, $(C_1-C_6)$alkylamino, $((C_1-C_6)$alkyl$)_2$amino, $(C_5-C_9)$heteroaryl, $(C_2-C_9)$heterocycloalkyl, $(C_3-C_9)$cycloalkyl or $(C_6-C_{10})$aryl; or $R^2$ and $R^3$ are each independently $(C_3-C_{10})$cycloalkyl, $(C_3-C_{10})$cycloalkoxy, $(C_1-C_6)$alkylamino, $((C_1-C_6)$alkyl$)_2$amino, $(C_6-C_{10})$arylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfonyl, $(C_6-C_{10})$arylsulfonyl, $(C_1-C_6)$acyl, $(C_1-C_6)$alkoxy-CO—NH—, $(C_1-C_6)$alkylamino-CO—, $(C_5-C_9)$heteroaryl, $(C_2-C_9)$heterocycloalkyl or $(C_6-C_{10})$aryl wherein the heteroaryl, heterocycloalkyl and aryl groups are optionally substituted by one to three halo, $(C_1-C_6)$alkyl, $(C_1-C_6)$alkyl-CO—NH—, $(C_1-C_6)$alkoxy-CO—NH—, $(C_1-C_6)$alkyl-CO—NH—$(C_1-C_6)$alkyl, $(C_1-C_6)$alkoxy-CO—NH—$(C_1-C_6)$alkyl, $(C_1-C_6)$alkoxy-CO—NH—$(C_1-C_6)$alkoxy, carboxy, carboxy$(C_1-C_6)$alkyl, carboxy$(C_1-C_6)$alkoxy, benzyloxycarbonyl$(C_1-C_6)$alkoxy, $(C_1-C_6)$alkoxycarbonyl$(C_1-C_6)$alkoxy, $(C_6-C_{10})$aryl, amino, amino$(C_1-C_6)$alkyl, $(C_1-C_6)$alkoxycarbonylamino, $(C_6-C_{10})$aryl$(C_1-C_6)$alkoxycarbonylamino, $(C_1-C_6)$alkylamino, $((C_1-C_6)$alkyl$)_2$amino, $(C_1-C_6)$alkylamino$(C_1-C_6)$alkyl, $((C_1-C_6)$alkyl$)_2$amino$(C_1-C_6)$alkyl, hydroxy, $(C_1-C_6)$alkoxy, carboxy, carboxy$(C_1-C_6)$alkyl, $(C_1-C_6)$alkoxycarbonyl, $(C_1-C_6)$alkoxycarbonyl$(C_1-C_6)$alkyl, $(C_1-C_6)$alkoxy-CO—NH—, $(C_1-C_6)$alkyl-CO—NH—, cyano, $(C_5-C_9)$heterocycloalkyl, amino-CO—NH—, $(C_1-C_6)$alkylamino-CO—NH—, $((C_1-C_6)$alkyl$)_2$amino-CO—NH—, $(C_6-C_{10})$arylamino-CO—NH—, $(C_5-C_9)$heteroarylamino-CO—NH—, $(C_1-C_6)$alkylamino-CO—NH—$(C_1-C_6)$alkyl, $((C_1-C_6)$alkyl$)_2$amino-CO—NH—$(C_1-C_6)$alkyl, $(C_6-C_{10})$arylamino-CO—NH—$(C_1-C_6)$alkyl, $(C_5-C_9)$heteroarylamino-CO—NH—$(C_1-C_6)$alkyl, $(C_1-C_6)$alkylsulfonyl, $(C_1-C_6)$alkylsulfonylamino, $(C_1-C_6)$alkylsulfonylamino$(C_1-C_6)$alkyl, $(C_6-C_{10})$arylsulfonyl, $(C_6-C_{10})$arylsulfonylamino, $(C_6-C_{10})$arylsulfonylamino$(C_1-C_6)$alkyl, $(C_1-C_6)$alkylsulfonylamino, $(C_1-C_6)$alkylsulfonylamino$(C_1-C_6)$alkyl, $(C_5-C_9)$heteroaryl or $(C_2-C_9)$heterocycloalkyl.

In certain embodiments in the compound of formula I, the Janus Kinase inhibitor is selected from the group consisting of:

Methyl-[4-methyl-1-(propane-1-sulfonyl)-piperidin-3-yl]-(7H-pyrrolo[2,3-d]pyrimidin-4-yl)-amine;
4-Methyl-3-[methyl-(7H-pyrrolo[2,3-d]pyrimidin-4-yl)-amino]-piperidine-1-carboxylic acid methyl ester;
3,3,3-Trifluoro-1-{4-methyl-3-[methyl-(7H-pyrrolo[2,3-d]pyrimidin-4-yl)-amino]-piperidin-1-yl}-propan-1-one;
4-Methyl-3-[methyl-(7H-pyrrolo[2,3-d]pyrimidin-4-yl)-amino]-piperidine-1-carboxylic acid dimethylamide;
({4-Methyl-3-[methyl-(7H-pyrrolo[2,3-d]pyrimidin-4-yl)-amino]-piperidine-1-carbonyl}-amino)-acetic acid ethyl ester;
3-{4-Methyl-3-[methyl-(7H-pyrrolo[2,3-d]pyrimidin-4-yl)-amino]-piperidin-1-yl}-3-oxo-propionitrile;
3,3,3-Trifluoro-1-{4-methyl-3-[methyl-(5-methyl-7H-pyrrolo[2,3-d]pyrimidin-4-yl)-amino]-piperidin-1-yl}-propan-1-one;
1-{4-Methyl-3-[methyl-(7H-pyrrolo[2,3-d]pyrimidin-4-yl)-amino]-piperidin-1-yl}-but-3-yn-1-one;
1-{3-[(5-Chloro-7H-pyrrolo[2,3-d]pyrimidin-4-yl)-methyl-amino]-4-methyl-piperidin-1-yl}-propan-1-one;
1-{3-[(5-Fluoro-7H-pyrrolo[2,3-d]pyrimidin-4-yl)-methyl-amino]-4-methyl-piperidin-1-yl}-propan-1-one;
N-cyano-4-methyl-3-[methyl-(7H-pyrrolo[2,3-d]pyrimidin-4-yl)-amino]-N'-propyl-piperidine-1-carboxamidine;
N-cyano-4,N',N'-Trimethyl-3-[methyl-(7H-pyrrolo[2,3-d]pyrimidin-4-yl)-amino]-piperidine-1-carboxamidine;
Methyl-[(3R,4R)-4-methyl-1-(propane-1-sulfonyl)-piperidin-3-yl]-(7H-pyrrolo[2,3-d]pyrimidin-4-yl)-amine;
(3R,4R)-)-4-Methyl-3-[methyl-(7H-pyrrolo[2,3-d]pyrimidin-4-yl)-amino]-piperidine-1-carboxylic acid methyl ester;
3,3,3-Trifluoro-1-{(3R,4R)-4-methyl-3-[methyl-(7H-pyrrolo[2,3-d]pyrimidin-4-yl)-amino]-piperidin-1-yl}-propan-1-one;
(3R,4R)-4-Methyl-3-[methyl-(7H-pyrrolo[2,3-d]pyrimidin-4-yl)-amino]-piperidine-1-carboxylic acid dimethylamide;
{(3R,4R)-4-Methyl-3-[methyl-(7H-pyrrolo[2,3-d]pyrimidin-4-yl)-amino]-piperidine-1-carbonyl}-amino)-acetic acid ethyl ester;
3-{(3R,4R)-4-Methyl-3-[methyl-(7H-pyrrolo[2,3-d]pyrimidin-4-yl)-amino]-piperidin-1-yl}-3-oxo-propionitrile;

3,3,3-Trifluoro-1-{(3R,4R)-4-methyl-3-[methyl-(5-methyl-7H-pyrrolo[2,3-d]pyrimidin-4-yl)-amino]-piperidin-1-yl}-propan-1-one;

1-{(3R,4R)-4-Methyl-3-[methyl-(7H-pyrrolo[2,3-d]pyrimidin-4-yl)-amino]-piperidin-1-yl}-but-3-yn-1-one;

1-{(3R,4R)-3-[(5-Chloro-7H-pyrrolo[2,3-d]pyrimidin-4-yl)-methyl-amino]-4-methyl-piperidin-1-yl}-propan-1-one;

1-{(3R,4R)-3-[(5-Fluoro-7H-pyrrolo[2,3-d]pyrimidin-4-yl)-methyl-amino]-4-methyl-piperidin-1-yl}-propan-1-one;

(3R,4R)—N-cyano-4-methyl-3-[methyl-(7H-pyrrolo[2,3-d]pyrimidin-4-yl)-amino]-N'-propyl-piperidine-1-carboxamidine; and (3R,4R)—N-cyano-4,N',N'-Trimethyl-3-[methyl-(7H-pyrrolo[2,3-d]pyrimidin-4-yl)-amino]-piperidine-1-carboxamidine, or a pharmaceutically acceptable salt thereof.

In certain embodiments, the Janus Kinase inhibitor is 3-{4-Methyl-3-[methyl-(7H-pyrrolo[2,3-d]pyrimidin-4-yl)-amino]-piperidin-1-yl}-3-oxo-propionitrile or a pharmaceutically acceptable salt thereof.

In certain embodiments, the Janus Kinase inhibitor is 3-{(3R,4R)-4-Methyl-3-[methyl-(7H-pyrrolo[2,3-d]pyrimidin-4-yl)-amino]-piperidin-1-yl}-3-oxo-propionitrile or a pharmaceutically acceptable salt thereof.

In certain embodiments the pharmaceutically acceptable salt of 3-{4-Methyl-3-[methyl-(7H-pyrrolo[2,3-d]pyrimidin-4-yl)-amino]-piperidin-1-yl}-3-oxo-propionitrile and/or 3-{(3R,4R)-4-Methyl-3-[methyl-(7H-pyrrolo[2,3-d]pyrimidin-4-yl)-amino]-piperidin-1-yl}-3-oxo-propionitrile is a citrate salt, such as a mono citrate salt. In certain embodiments, such compounds are crystalline, as discussed in U.S. Pat. No. 6,965,027, the contents of which are hereby incorporated here by reference.

The Janus Kinase inhibitors of the present disclosure can be in the form of a pharmaceutically acceptable acid addition salt. The acids which are used to prepare the pharmaceutically acceptable acid addition salts of the aforementioned base compounds of this disclosure are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The Janus Kinase inhibitors of the present disclosure can be in the form of a pharmaceutically acceptable base addition salt. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Certain of the Janus Kinase inhibitors mentioned here are basic in nature are capable of forming a wide variety of different salts with various inorganic and organic acids. Although such salts must be pharmaceutically acceptable for administration to animals, it is often desirable in practice to initially isolate the compound of the present disclosure from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this disclosure are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Certain of the Janus Kinase inhibitors mentioned here are acidic in nature, and are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this disclosure are those which form non-toxic base salts with the acidic compounds of the present disclosure. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

In certain embodiments, the Janus Kinase inhibitor is a compound specified and/or exemplified in U.S. Pat. No. 6,635,762; U.S. Publication No. 2004-0058922A1; U.S. Pat. No. 6,610,847; U.S. Pat. No. 6,890,929; U.S. Publication No. 2005-0171128; U.S. Pat. No. 6,627,754; U.S. Pat. No. 6,956,041; U.S. Pat. No. 7,091,208; U.S. Pat. No. 6,696,567; U.S. Pat. No. 6,962,993; U.S. Publication No. 2005-0197349; U.S. Publication No. 2003-0073719A1; U.S. Publication No. 2004-0229923 A1; U.S. Pat. No. 6,965,027; U.S. Publication No. 2005-0159434A1, the contents of all of which are hereby incorporated herein by reference.

The Janus Kinase inhibitors as used in the combination therapy of the present disclosure include all conformational isomers (e.g., cis and trans isomers) and mixtures thereof. Such compounds have asymmetric centers readily apparent to those of skill in the art and therefore exist in different enantiomeric and diastereomeric forms. This disclosure relates to the use of all optical isomers and stereoisomers of such compounds used in the present disclosure, and mixtures thereof, and to all pharmaceutical compositions and methods of treatment that may employ or contain them. In this regard, this disclosure includes both the E and Z configurations. In particular, resolution of racemic mixtures of enantiomers of compounds, used in providing the $R^1$ substituent of formula I, is effected by treating the racemic mixture of the compound of formula $HNR^4R^5$, e.g., a compound of formula III below, with a specific optical isomer of a disubstituted tartaric acid or tartrate in an appropriate solvent such as ethanol with or without water as a co-solvent. The desired enantiomer can be obtained in excess of 90% using such methods disclosed in U.S. Ser. No. 10/154,699, the contents of which are hereby incorporated herein by reference for all purposes. Specific resolving agents useful in said resolution include optical isomers of tartaric acid and tartaric acid derivatives such as di-p-toluoyl-L-tartaric acid and (S)-(+)-Andeno acid (pencyphos, (S)-(+)-2-hydroxy-5,5-dimethyl-4-phenyl-1,3,2-dioxyphosphorinane-2-oxide) salt. Of course, those of skill in the art given the benefit of the present disclosure will appreciate other suitable resolving agents potentially useful for resolving such compounds of formula $HNR^4R^5$.

The Janus Kinase inhibitors as used in the combination therapy of the present disclosure may also exist as tautomers. This disclosure relates to the use of all such tautomers and mixtures thereof.

Interaction between antipodes of the resolving material and specific enantiomer provides a resolution of the racemic mixture whereby a precipitate of the resolving material and enantiomer provides one of the desired stereospecific materials and wherein the remaining enantiomer in solution can be separately isolated thereby. Thus, depending on the specific enantiomer desired and the separation method to be used (i.e., from precipitate or solution), the stereospecific nature of the resolving nature can be concomitantly selected; e.g. an "L" form of the resolving agent such as a tartrate derivative provides a precipitate of an "R" form of the $R^1$ substituent and a solution containing the "L" form and vice versa.

The aforementioned resolving agents are effective in providing a 3R,4R enantiomer of the compound of the formula III (either in precipitate or solution, as described):

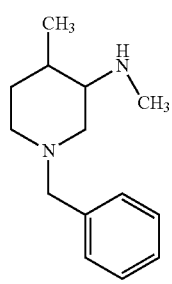

III

In certain embodiments, resolution of the compound of formula III is effected by the steps of:

a) mixing a racemic mixture of the compound of formula III in an appropriate solution with a resolving compound, having a defined stereospecificity, for a time sufficient to allow substantial precipitation of a stereospecific isomer of the racemic mixture from the solution;

b) depending on the stereospecific form of the compound which is desired, collecting either the precipitate and purifying it or collecting the mother liquor and recrystallizing the enantiomer contained therein.

With some materials a slurry rather than a solution is formed with the resolution of the present disclosure involving a slurry to slurry conversion. The term "solution" encompasses both a solution and a slurry.

The temperature at which the resolution and precipitation is effected is preferably ambient temperature and while precipitation time is not restricted for efficiency the time is preferably no more than about four hours. In order to facilitate the resolution it is desirable to use enantiomers in the racemic mixture which are in a stable form and the compound of formula II is most stable in acid addition salt form such as a hydrochloride salt, rather than a free base form and it is preferred that the racemic compound mixture be accordingly converted prior to resolution. Thus, for example, formation of the hydrochloride salt of the compound of formula II is effected preferably in ethanol with a small amount of toluene as cosolvent. Alternatively, methanol, isopropanol, acetonitrile, or tetrahydrofuran (or mixtures thereof with or without water as a cosolvent) with cosolvents of toluene, ethylacetate, dichloromethane, dichloroethane, or tetrahydrofuran may be used in the salt formation. The HCl salt is particularly preferred since this form provides a superior purification and enriched of other stereoisomers from the prior step.

A preferred displacement solvent used in the resolution is ethyl acetate. Toluene, acetonitrile, or heptanes are also useful as solvents.

A preferred isolation solvent is acetone. Other solvents useful in this regard include isopropanol, ethanol, methyl ethyl ketone, methyl isopropyl ketone, acetonitrile, and tetrahydrofuran. The solvents may also be used as cosolvents with each other or with water.

Preferred resolution compounds include tartaric acid and its derivatives such as toluoyl and benzoyl tartaric acids in stereospecific conformation, as described. Other resolution compounds include stereospecific adeno acid and derivatives thereof.

To facilitate precipitation and recrystallization addition of seeds is optional, but preferred in order to obtain higher ee material with fewer recrystallizations.

This disclosure also encompasses pharmaceutical compositions containing prodrugs of the Janus Kinase inhibitors of the present disclosure such as the compounds of the formula I and the use of such prodrugs in the presently disclosed pharmaceutical combination therapies. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

Preparation A

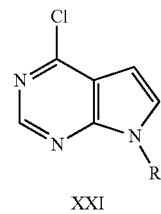

XXI

↓1

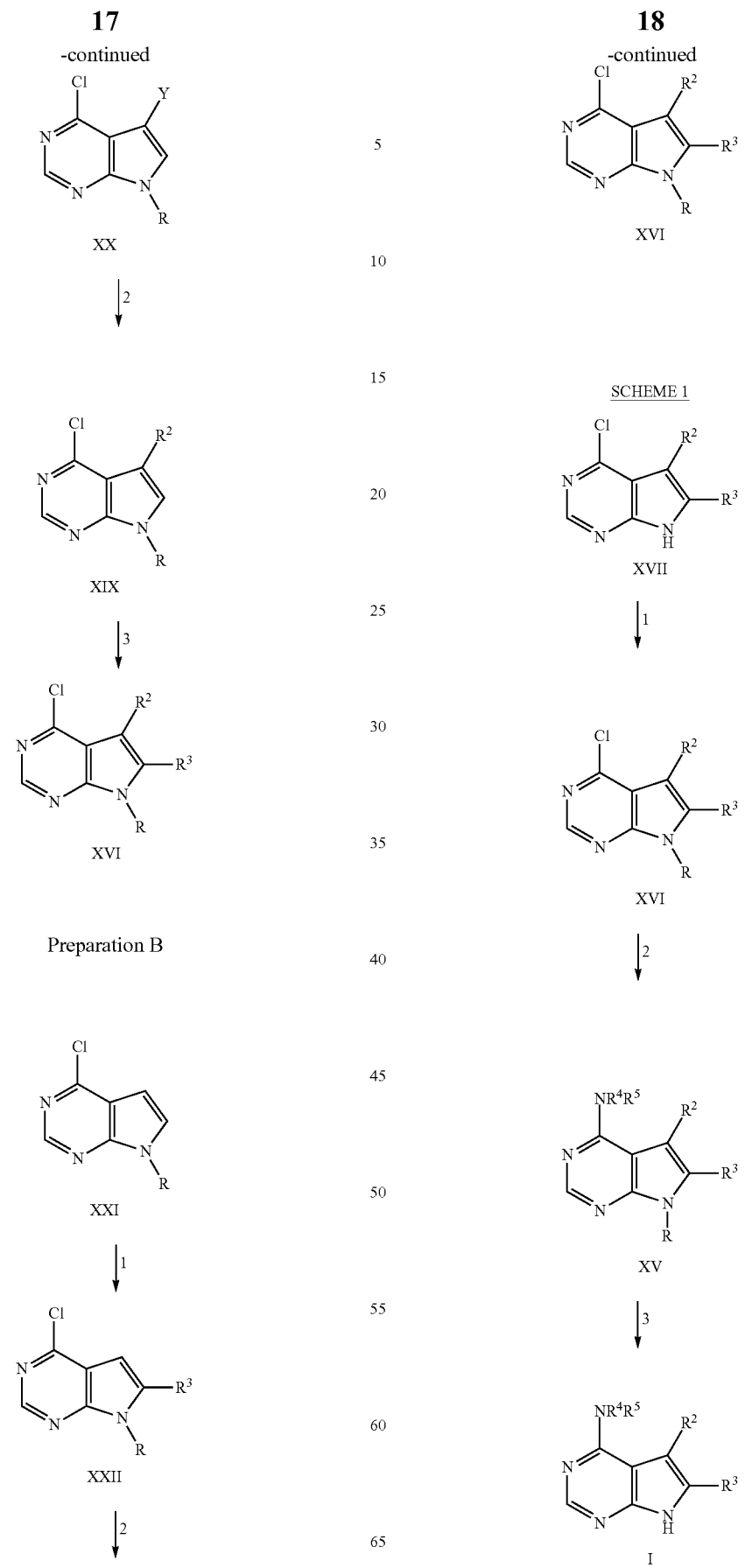

SCHEME 2

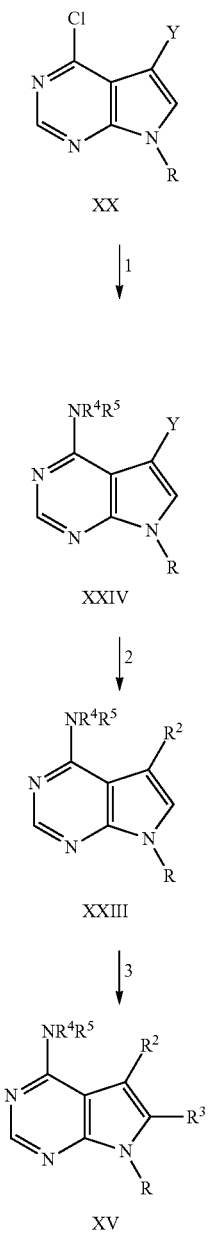

SCHEME 3

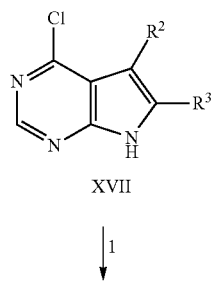

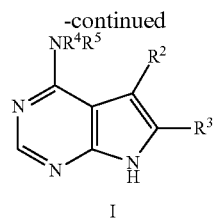

In reaction 1 of Preparation A, the 4-chloropyrrolo[2,3-d]pyrimidine compound of formula XXI, wherein R is hydrogen or a protecting group such as benzenesulfonyl or benzyl, is converted to the 4-chloro-5-halopyrrolo[2,3-d]pyrimidine compound of formula XX, wherein Y is chloro, bromo or iodo, by reacting XXI with N-chlorosuccinimide, N-bromosuccinimide or N-iodosuccinimide. The reaction mixture is heated to reflux, in chloroform, for a time period between about 1 hour to about 3 hours, preferably about 1 hour. Alternatively, in reaction 1 of Preparation A, the 4-chloropyrrolo[2,3-d]pyrimidine of formula XXI, wherein R is hydrogen, is converted to the corresponding 4-chloro-5-nitropyrrolo[2,3-d]pyrimidine of formula XX, wherein Y is nitro, by reacting XXI with nitric acid in sulfuric acid at a temperature between about −10° C. to about 10° C., preferably about 0° C., for a time period between about 5 minutes to about 15 minutes, preferably about 10 minutes. The compound of formula XXI, wherein Y is nitro, is converted to the corresponding 4-chloro-5-aminopyrrolo[2,3-d]pyrimidine of the formula XX, wherein Y is amino, by reacting XXI under a variety of conditions known to one skilled in the art such as palladium hydrogenolysis or tin(IV)chloride and hydrochloric acid.

In reaction 2 of Preparation A, the 4-chloro-5-halopyrrolo[2,3-d]pyrimidine compound of formula XX, wherein R is hydrogen, is converted to the corresponding compound of formula XIX, wherein $R^2$ is $(C_1-C_6)$alkyl or benzyl, by treating XX with N-butyllithium, at a temperature of about −78° C., and reacting the dianion intermediate so formed with an alkylhalide or benzylhalide at a temperature between about −78° C. to room temperature, preferably room temperature. Alternatively, the dianion so formed is reacted with molecular oxygen to form the corresponding 4-chloro-5-hydroxypyrrolo[2,3-d]pyrimidine compound of formula XIX, wherein $R^2$ is hydroxy. The compound of formula XX, wherein Y is bromine or iodine and R is benzenesulfonate, is converted to the compound of formula XIX, wherein $R^2$ is $(C_6-C_{12})$aryl or vinyl, by treating XX with N-butyllithium, at a temperature of about −78° C., followed by the addition of zinc chloride, at a temperature of about −78° C. The corresponding organo zinc intermediate so formed is then reacted with aryliodide or vinyl iodide in the presence of a catalytic quantity of palladium. The reaction mixture is stirred at a temperature between about 50° C. to about 80° C., preferably about 70° C., for a time period between about 1 hour to about 3 hours, preferably about 1 hour.

In reaction 3 of Preparation A, the compound of formula XIX is converted to the corresponding compound of formula XVI by treating XIX with N-butyllithium, lithium diisopropylamine or sodium hydride, at a temperature of about −78° C., in the presence of a polar aprotic solvent, such as tetrahydrofuran. The anionic intermediate so formed is further reacted with (a) alkylhalide or benzylhalide, at a temperature between about −78° C. to room temperature, preferably −78° C., when $R^3$ is alkyl or benzyl; (b) an aldehyde or ketone, at a temperature between about −78° C. to room temperature, preferably −78° C., when $R^3$ is alkoxy; and (c) zinc chloride, at a temperature between about −78° C. to room temperature, preferably −78° C., and the corresponding organozinc intermediate so formed is then reacted with aryliodide or vinyl iodide in the presence of a catalytic quantity of palladium. The resulting reaction mixture is stirred at a temperature between about 50° C. to about 80° C., preferably about 70° C., for a time period between about 1 hour to about 3 hours, preferably about 1 hour. Alternatively, the anion so formed is reacted with molecular oxygen to form the corresponding 4-chloro-6-hydroxypyrrolo[2,3-d]pyrimidine compound of formula XVI, wherein $R^3$ is hydroxy.

In reaction 1 of Preparation B, the 4-chloropyrrolo[2,3-d]pyrimidine compound of formula XXI is converted to the corresponding compound of formula XXII, according to the procedure described above in reaction 3 of Preparation A.

In reaction 2 of Preparation B, the compound of formula XXII is converted to the corresponding compound of formula XVI, according to the procedures described above in reactions 1 and 2 of Preparation A.

In reaction 1 of Scheme 1, the 4-chloropyrrolo[2,3-d]pyrimidine compound of formula XVII is converted to the corresponding compound of formula XVI, wherein R is benzenesulfonyl or benzyl, by treating XVII with benzenesulfonyl chloride, benzylchloride or benzylbromide in the presence of a base, such as sodium hydride or potassium carbonate, and a polar aprotic solvent, such as dimethylformamide or tetrahydrofuran. The reaction mixture is stirred at a temperature between about 0° C. to about 70° C., preferably about 30° C., for a time period between about 1 hour to about 3 hours, preferably about 2 hours.

In reaction 2 of Scheme 1, the 4-chloropyrrolo[2,3-d]pyrimidine compound of formula XVI is converted to the corresponding 4-aminopyrrolo[2,3-d]pyrimidine compound of formula XV by coupling XVI with an amine of the formula $HNR^4R^5$. In certain embodiments, the 4-chloropyrrolo[2,3-d]pyrimidine compound of formula XVI is coupled with the enantiomer obtained with the resolution of $NHR^4R^5$, i.e. a single stereoisomer of formula III, to arrive at the corresponding 4-aminopyrrolo[2,3-d]pyrimidine compound of formula XV, which has the same stereochemistry as the resolved reactant of formula $NHR^4R^5$. That is, the coupling reaction 2 in such embodiments proceeds without inversion or loss of stereochemistry and instead proceeds with retention of stereochemistry. Such lack of inversion or loss of stereochemistry and retention of stereochemistry continues for the remainder of the synthesis described below to arrive at the compounds of formula I. The reaction is carried out in an alcohol solvent, such as tert-butanol, methanol or ethanol, or other high boiling organic solvents, such as dimethylformamide, triethylamine, 1,4-dioxane or 1,2-dichloroethane, at a temperature between about 60° C. to about 120° C., preferably about 80° C. Typical reaction times are between about 2 hours to about 48 hours, preferably about 16 hours. When $R^5$ is a nitrogen containing heterocycloalkyl group, each nitrogen must be protected by a protecting group, such a benzyl. Removal of the $R^5$ protecting group is carried out under conditions appropriate for that particular protecting group in use which will not affect the R protecting group on the pyrrolo[2,3-d]pyrimidine ring. Removal of the $R^5$ protecting group, when benzyl, is carried out in an alcohol solvent, such as ethanol, in the presence of hydrogen and a catalyst, such as palladium hydroxide on carbon. The $R^5$ nitrogen containing heterocycloalkyl group so formed may be further reacted with a variety of different electrophiles of formula II. For urea formation, electrophiles of formula II such as isocyanates, carbamates and carbamoyl chlorides are reacted with the $R^5$ nitrogen of the heteroalkyl group in a solvent, such as acetonitrile or dimethylformamide, in the presence of a base, such as sodium or potassium carbonate, at a temperature between about 20° C. to about 100° C. for a time period between about 24 hours to about 72 hours. For amide and sulfonamide formation, electrophiles of formula II, such as acylchlorides and sulfonyl chlorides, are reacted with the $R^5$ nitrogen of the heteroalkyl group in a solvent such as methylene chloride in the presence of a base such as pyridine at ambient temperatures for a time period between about 12 hours to about 24 hours. Amide formation may also be carried out by reacting a carboxylic acid with the heteroalkyl group in the presence of a carbodiimide such as 1-(3-dimethylaminopropyl)-3-ethylcarbodiimide in a solvent such as methylene chloride at ambient temperatures for 12-24 hours. For alkyl formation, electrophiles of formula II, such as α,β-unsaturated amides, acids, nitriles, esters, and α-halo amides, are reacted with the $R^5$ nitrogen of the heteroalkyl group in a solvent such as methanol at ambient temperatures for a time period between about 12 hours to about 18 hours. Alkyl formation may also be carried out by reacting aldehydes with the heteroalkyl group in the presence of a reducing agent, such as sodium cyanoborohydride, in a solvent, such as methanol, at ambient temperature for a time period between about 12 hours to about 18 hours.

In reaction 3 of Scheme 1, removal of the protecting group from the compound of formula XV, wherein R is benzenesulfonyl, to give the corresponding compound of formula I, is carried out by treating XV with an alkali base, such as sodium hydroxide or potassium hydroxide, in an alcohol solvent, such as methanol or ethanol, or mixed solvents, such as alcohol/tetrahydrofuran or alcohol/water. The reaction is carried out at room temperature for a time period between about 15 minutes to about 1 hour, preferably 30 minutes. Removal of the protecting group from the compound of formula XV, wherein R is benzyl, is conducted by treating XV with sodium in ammonia at a temperature of about −78° C. for a time period between about 15 minutes to about 1 hour.

In reaction 1 of Scheme 2, the 4-chloropyrrolo[2,3-d]pyrimidine compound of formula XX is converted to the corresponding 4-aminopyrrolo[2,3-d]pyrimidine compound of formula XXIV, according to the procedure described above in reaction 2 of Scheme 1.

In reaction 2 of Scheme 2, the 4-amino-5-halopyrrolo[2,3-d]pyrimidine compound of formula XXIV, wherein R is benzenesulfonate and Z is bromine or iodine, is converted to the corresponding compound of formula XXII by reacting XXIV with (a) arylboronic acid, when $R^2$ is aryl, in an aprotic solvent, such tetrahydrofuran or dioxane, in the presence of a catalytic quantity of palladium (0) at a temperature between about 50° C. to about 100° C., preferably about 70° C., for a time period between about 2 hours to about 48 hours, preferably about 12 hours; (b) alkynes, when $R^2$ is alkynyl, in the presence of a catalytic quantity of copper (I) iodide and palladium (0), and a polar solvent, such as dimethylformamide, at room temperature, for a time period between about 1 hour to about 5 hours, preferably about 3 hours; and (c) alkenes or styrenes, when $R^2$ is vinyl or styrenyl, in the presence of a catalytic quantity of palladium in dimethylformamide, dioxane or tetrahydrofuran, at a temperature between about 80° C. to about 100° C., preferably about 100° C., for a time period between about 2 hours to about 48 hours, preferably about 48 hours.

In reaction 3 of Scheme 2, the compound of formula XXIII is converted to the corresponding compound of formula XV, according to the procedure described above in reaction 3 of Preparation A.

In reaction 1 of Scheme 3, the compound of formula XVII is converted to the corresponding compound of formula I, according to the procedure described above in reaction 2 of Scheme 1.

In certain embodiments, the HMG-CoA reductase inhibitor is a statin. HMG CoA reductase catalyzes the conversion of HMG CoA to mevalonate, which is an early and rate-limiting step in the biosynthesis of cholesterol. Compounds that inhibit the activity of HMG CoA reductase can be readily identified by using assays well known in the art; see, as examples, the assays described or cited in U.S. Pat. No. 4,231,938 at column 6, and in International Patent Publication WO 84/02131 at pp. 30-33.

In other embodiments, the statin is selected from the group consisting of atorvastatin, fluvastatin, lovastatin, pravastatin, simvastatin, cerivastatin, rivastatin, mevastatin, velostatin, compactin, dalvastatin, fluindostatin, rosuvastatin, pitivastatin, and dihydrocompactin. In some embodiments, the statin is atorvastatin. In another embodiments, the statin is atorvastatin calcium salt. Examples of useful statins include atorvastatin, simvastatin, pravastatin, cerivastatin, mevastatin (see U.S. Pat. No. 3,883,140), velostatin (also called synvinolin; see U.S. Pat. Nos. 4,448,784 and 4,450,171), fluvastatin, lovastatin, dalvastatin, rosuvastatin and fluindostatin (Sandoz XU-62-320), dalvastain (EP Appln. PubIn. No. 738510), and pharmaceutically acceptable salts thereof.

Atorvastatin calcium is marketed under the tradename "LIPITOR" (see U.S. Pat. No. 5,273,995).

Simvastatin calcium is marketed under the tradename "ZOCOR" (see U.S. Pat. No. 4,444,784), Pravastatin sodium is marketed under the tradename "PRAVACHOL" (see U.S. Pat. No. 4,346,227), Cerivastatin sodium is marketed under the tradename "BAYCHOL" (also called rivastatin; see U.S. Pat. No. 5,502,199), Fiuvastatin sodium is marketed under the tradename "LESCOL" (see U.S. Pat. No. 5,354,772).

Lovastatin is marketed under the tradename "MEVACOR" (see U.S. Pat. No. 4,231,938).

Rosuvastatin is marketed under the tradename "CRESTOROR".

The compositions of the present disclosure may be formulated in a conventional manner using one or more pharmaceutically acceptable carriers. The pharmaceutically acceptable carrier can be any such carrier known in the art including those described in, for example, *Remington's Pharmaceutical Sciences*, Mack Publishing Co., (A. R. Gennaro edit. 1985). Pharmaceutical compositions of the compounds presently disclosed may be prepared by conventional means known in the art including, for example, mixing at least one presently disclosed compound with a pharmaceutically acceptable carrier.

The compounds presently disclosed may also be formulated for sustained delivery according to methods well known to those of ordinary skill in the art. Examples of such formulations can be found in U.S. Pat. Nos. 3,119,742, 3,492,397, 3,538,214, 4,060,598, and 4,173,626.

Thus, the active compounds of the disclosure may be formulated for oral, buccal, intranasal, parenteral (e.g., intravenous, intramuscular or subcutaneous), rectal administration, in a form suitable for administration by inhalation or insufflation, or the active compounds may be formulated for topical administration.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be CoAted by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

For intranasal administration or administration by inhalation, the active compounds of the disclosure are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the disclosure and a suitable powder base such as lactose or starch.

The active compounds of the disclosure may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the disclosure may also be formulated in rectal compositions such as suppositories or retention enemas, e.g., containing conventional suppository bases such as cocoa butter or other glycerides.

For topical administration, a presently disclosed compound may be formulated as an ointment or cream.

Typically, combinations of the Janus Kinase inhibitors and the HMG-CoA reductase inhibitor are administered in a therapeutically effective amount in the pharmaceutical combination therapies and associated methods disclosed herein, the amount of which is readily apparent to those of skill in the art to achieve the desired pharmacological and/or physiological effect. In certain embodiments, the Janus Kinase inhibitor or a pharmaceutically acceptable salt thereof (sometimes referred to herein as "the active compounds") is administered in a dose of 0.1 to 1000 mg of the active ingredient per unit dose which could be administered, for example, 1 to 4 times per day. The dosage level can vary either between one or more dosing regimens or within the same dosing regimen. In certain embodiments where the Janus Kinase inhibitor or a pharmaceutically acceptable salt thereof is administered orally, the dose for the active compounds can be in a range from 1 to 50 mg BID (i.e., twice a day) or from 5 to 20 mg QD (i.e., daily), and preferably 1 mg BID, 2 mg BID, 3 mg BID, 4 mg BID, 5 mg BID, 6 mg BID, 7 mg BID, 8 mg BID, 9 mg BID, 10 mg BID, 11 mg BID, 12 mg BID, 13 mg BID, 14 mg BID, 15 mg BID, 20 mg BID, 25 mg BID, or 30 mg BID, and preferably 0.25 mg BID, 0.5 mg BID, 1 mg BID, 5 mg BID, 10 mg BID, 20 mg BID, and more preferably 1 mg BID, 3 mg BID, 5 mg BID, 15 mg, BID, 20 mg QD.

In certain embodiments, the HMG-CoA reductase inhibitor is administered in a dose of 1 mg to 5 g (i.e., 5000 mg), e.g., 5 mg, 10 mg, 25 mg, 50 mg, 100 mg, 250 mg, 500 mg, 750 mg, 1000 mg, 1250 mg, 1500 mg, 1750 mg, 2000 mg, or combinations thereof. For each of the dosage amounts provided for the HMG-CoA reductase inhibitors, the HMG-CoA reductase inhibitor can be dosed twice a day, daily, weekly, etc. as would be apparent to those of skill in the art, e.g., a prescribed amount. Of course, other suitable dosage levels for the compounds of the disclosure and the HMG-CoA reductase inhibitors administered in a combination therapy will be readily apparent to those of skill in the art given the benefit of the present disclosure.

In certain embodiments, the mammal is a human.

In another embodiments, the Janus Kinase inhibitor or a pharmaceutically acceptable salt thereof and the HMG-CoA reductase inhibitor or a pharmaceutically acceptable salt thereof are administered simultaneously, sequentially or separately.

In some embodiments, the ratio of Janus Kinase inhibitor or a pharmaceutically acceptable salt thereof to the HMG-CoA reductase inhibitor or a pharmaceutically acceptable salt thereof is about 2:1 to about 1:40 w/w.

In other embodiments, the dosage form is selected from the group consisting of a solution, a suspension, a tablet, a pill, a sachet, a capsule, multiparticulates and a powder.

Aerosol formulations in the average adult human are preferably arranged so that each metered dose or "puff" of aerosol contains 20 μg to 1000 μg of the compound of the disclosure. The overall daily dose with an aerosol will be within the range 0.1 mg to 1000 mg. Administration may be several times daily, for example 2, 3, 4 or 8 times, giving for example, 1, 2 or 3 doses each time.

The ability of the compounds of formula I or their pharmaceutically acceptable salts to inhibit Janus Kinase 3 and, consequently, demonstrate their effectiveness for treating disorders or conditions characterized by Janus Kinase 3 is shown by the following in vitro assay tests.

The present invention also provides a pharmaceutical composition comprising a Janus Kinase inhibitor or a pharmaceutically acceptable salt thereof; and a HMG-CoA reductase inhibitor or a pharmaceutically acceptable salt thereof; and a pharmaceutically acceptable carrier.

The present invention also provides a method of treating a disease in a mammal, comprising administering to a mammal in need thereof a therapeutically effective amount of a Janus Kinase inhibitor and a HMG-CoA reductase inhibitor or a pharmaceutically acceptable salt thereof or a pharmaceutical composition.

In other embodiments, the disease is selected from the group consisting of atherosclerosis, myocardial infarction, hypocholesterolemia, hyperlipidemia, ischemic heart disease, congestive heart failure, acute coronary syndrome, plaque instability, coronary artery disease, cerebrovascular disease, peripheral vascular disease and cardiac risk management.

The present invention further provides a method of inhibiting cholesterol biosynthesis in a mammal, comprising administering to a mammal in need thereof a Janus Kinase inhibitor and a HMG-CoA reductase inhibitor or a pharmaceutically acceptable salt thereof or a pharmaceutical composition.

The present invention also provides a method of lowering blood cholesterol level in a mammal, comprising administering to a mammal in need thereof a Janus Kinase inhibitor and a HMG-CoA reductase inhibitor or a pharmaceutically acceptable salt thereof or a pharmaceutical composition.

The present invention further provides a kit for achieving a therapeutic effect in a mammal comprising: a therapeutically effective amount of a Janus Kinase inhibitor or a pharmaceutically acceptable salt thereof; and a therapeutically effective amount of a HMG-CoA reductase inhibitor or a pharmaceutically acceptable salt thereof; and a container.

Pharmaceutical Combination Therapies and Effects on Total Cholesterol Level

Efficacy Study:

In certain embodiments, the efficacy of the pharmaceutical combination therapy of TOFACITINIB (Janus Kinase inhibitor) and atorvastatin (HMG-CoA reductase inhibitor) or TOFACITINIB (Janus Kinase inhibitor) and placebo was evaluated.

At the enrollment visit, patients had a mean LDL-C of 111.99 mg/dL and 114.68 mg/dL in the atorvastatin/TOFACITINIB and the placebo/TOFACITINIB treatment groups, respectively. After 6 weeks treatment with TOFACITINIB the baseline LDL-C mean increased to 135.83 mg/dL and 138.26 mg/dL in the atorvastatin/TOFACITINIB and the placebo/TOFACITINIB treatment groups, respectively. At week 12, 6 weeks following randomization, the LDL-C mean had decreased to 84.03 mg/dL in the atorvastatin treated group compared to an increase in the mean LDL-C to 142.61 mg/dL in the placebo group.

The percent reduction from baseline in LDL-C level is significantly greater for patients who received atorvastatin compared with placebo at Week 12 (primary endpoint); adjusted mean reduction is −35.3% in atorvastatin group compared with 5.8% increase in placebo group, is shown in Table 1.

TABLE 1

Percent Change from Baseline in LDL (%)

| | TOFACITINIB 10 mg BID | |
| --- | --- | --- |
| | atorvastatin | placebo |
| Week 10 | | |
| N | 45 | 46 |
| Adjusted mean | −39.0 | 5.5 |
| Difference from placebo | −44.5 | |
| P-value | <.0001 | |
| Week 12* | | |
| N | 46 | 45 |
| Adjusted mean | −35.3 | 5.8 |
| Difference from placebo | −41.1 | |
| P-value | <.0001 | |

*Primary endpoint.
Source: Table 14.2.2.4

The trend of LDL-C level in each treatment group is presented in FIG. 1, which shows an increase in median LDL-C level after Enrollment Visit (introduction of TOFACITINIB treatment) in both treatment groups and then a decrease after Baseline Visit in the atorvastatin group to values below Enrollment Visit levels compared to a slightly increasing trend in the placebo group. Thus, FIG. 1 shows significant decrease in LDL level after baseline visit for patients who received pharmaceutical combination therapy of TOFACITINIB and atorvastatin.

Figure 2:
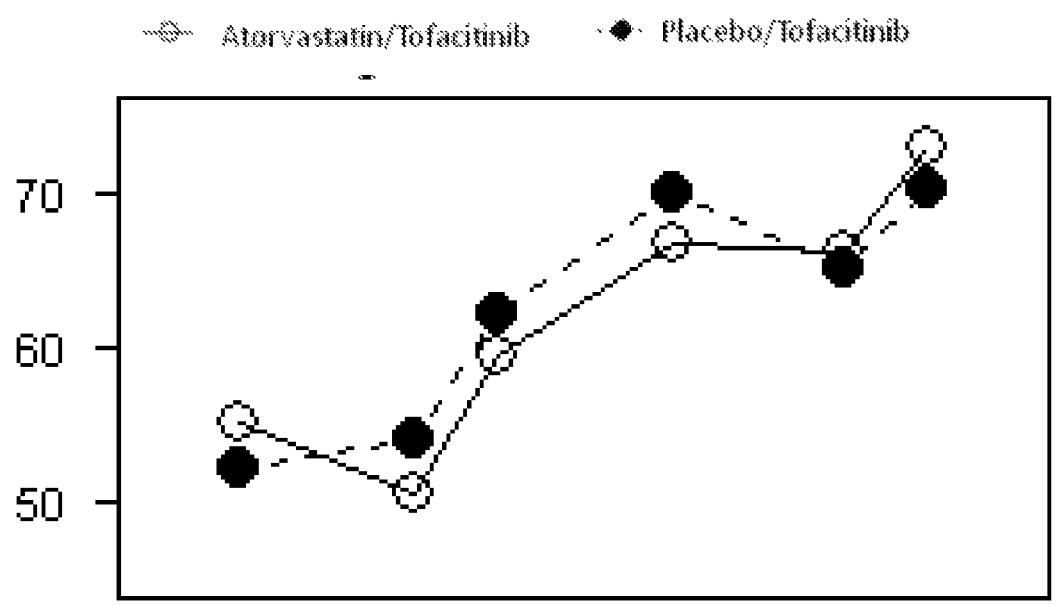
FIG. 2 shows increase in HDL level after baseline visit for patients who received pharmaceutical combination therapy of tofacitinib and atorvastatin.

HDL levels increase following the Enrollment Visit and continue a slight upward trend following Baseline visit in both the atorvastatin group and the placebo group through the end of the study. Thus, FIG. 2 shows significant increase in HDL level after baseline visit for patients who received pharmaceutical combination therapy of TOFACITINIB and atorvastatin.

Figure 3:
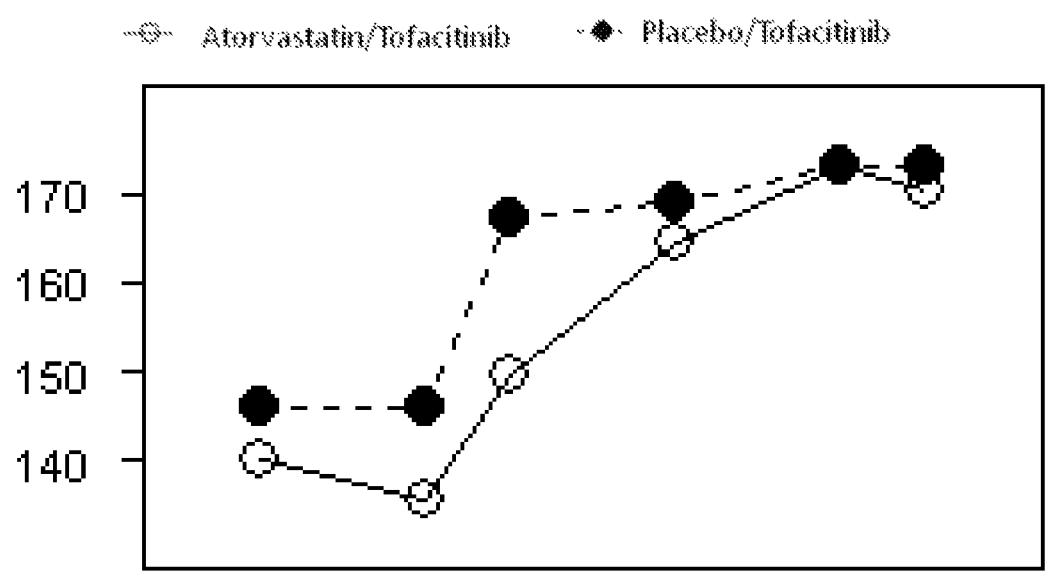
FIG. 3 shows increase in Apolipoprotein A-1 level after baseline visit for patients who received pharmaceutical combination therapy of tofacitinib and atorvastatin.

Apolipoprotein A-1 increases following introduction of TOFACITINIB treatment and seems to slightly trend upward in both treatment groups after Baseline through the end of the study. FIG. 3 shows increase in Apolipoprotein A-1 level after baseline visit for patients who received pharmaceutical combination therapy of TOFACITINIB and atorvastatin.

Figure 4:
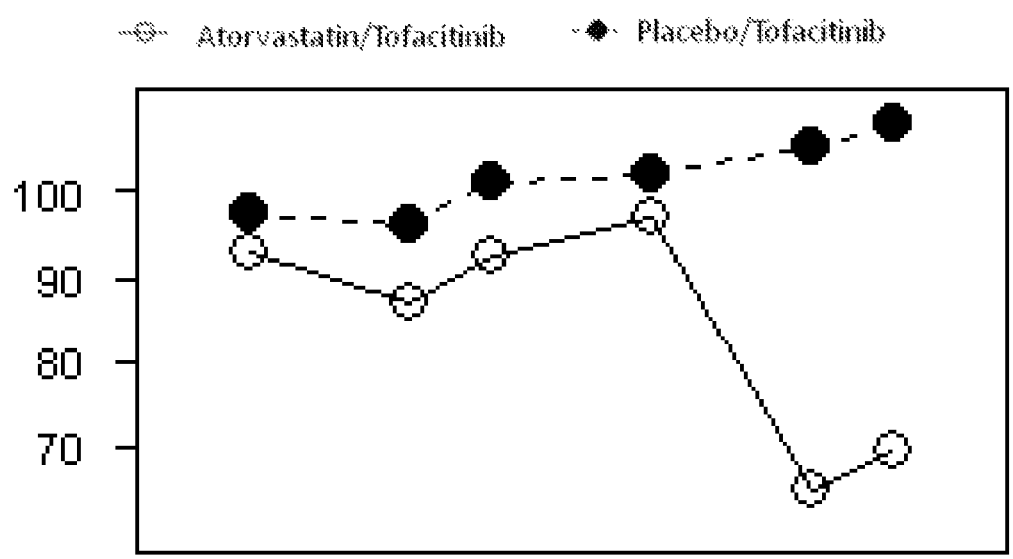
FIG. 4 shows decrease in Apolipoprotein B level after baseline visit for patients who received pharmaceutical combination therapy of tofacitinib and atorvastatin.

The trend of Apolipoprotein B level in each treatment group is presented in FIG. 4, which shows an increase in median Apolipoprotein B level after Enrollment Visit (introduction of TOFACITINIB treatment) in both treatment groups and then a decrease after Baseline Visit in the atorvastatin group to values below Enrollment Visit levels compared to a slightly increasing trend in the placebo group. FIG. 4 shows decrease in Apolipoprotein B level after baseline visit for patients who received pharmaceutical combination therapy of TOFACITINIB and atorvastatin.

Figure 5:
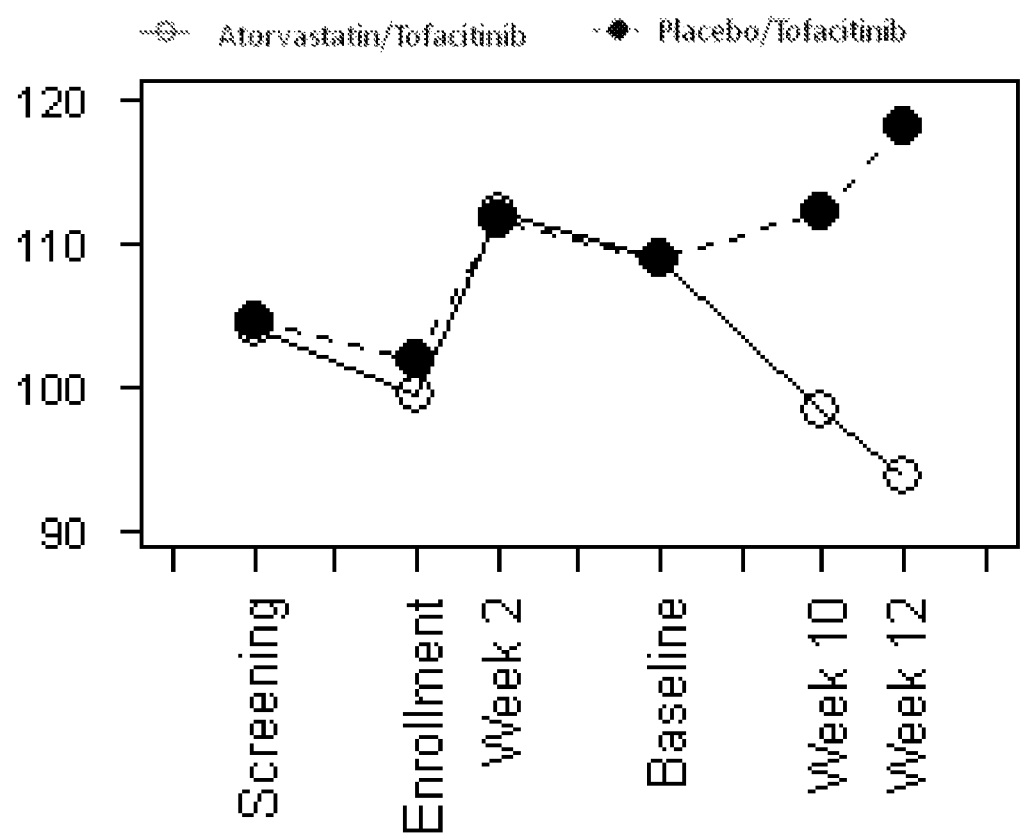
FIG. 5 shows decrease in triglycerides level after baseline visit for patients who received pharmaceutical combination therapy of tofacitinib and atorvastatin.

Triglycerides increase following introduction of TOFACITINIB treatment and decreases after Baseline Visit in the atorvastatin group while increases continue in the placebo group. Thus, FIG. 5 shows significant decrease in triglycerides level after baseline visit for patients who received pharmaceutical combination therapy of TOFACITINIB and atorvastatin.

Figure 6:
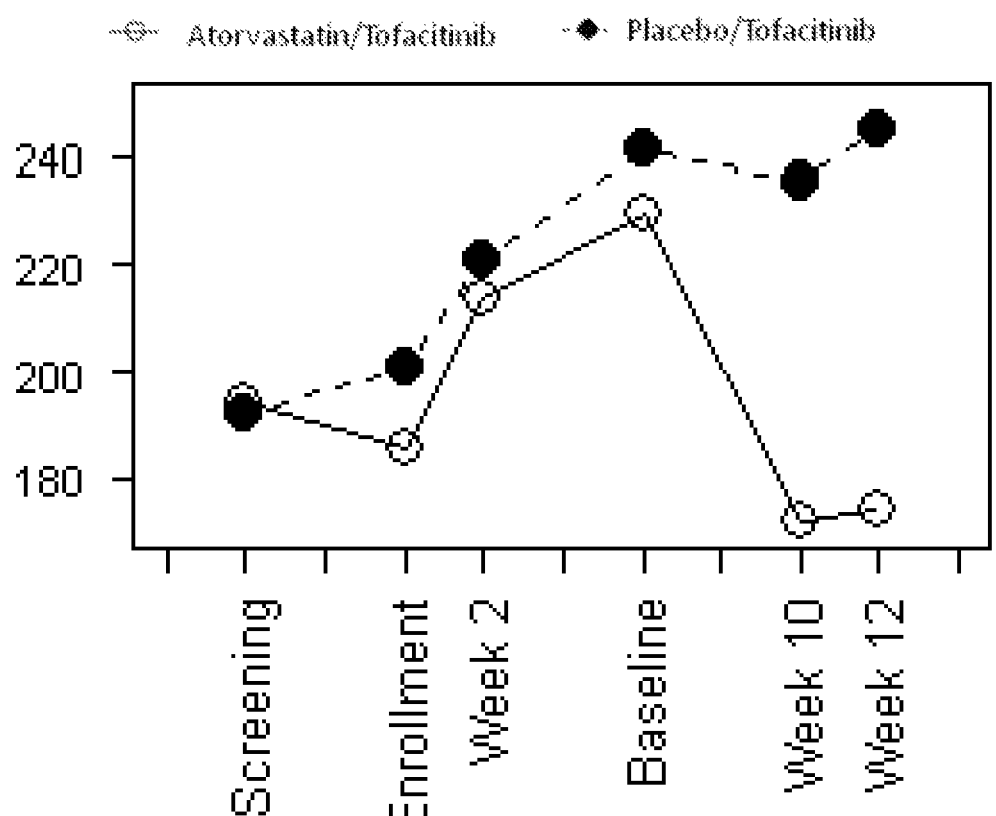
FIG. 6 shows decrease in total cholesterol level after baseline visit for patients who received pharmaceutical combination therapy of tofacitinib and atorvastatin.

The trend of total cholesterol level in each treatment group is presented in FIG. 6, which shows an increase in median total cholesterol level after Enrollment Visit (introduction of TOFACITINIB treatment) in both treatment groups and then a decrease after Baseline Visit in the atorvastatin group to values below Enrollment Visit levels compared to a slightly increasing trend in the placebo group. Thus, FIG. 6 shows significant decrease in total cholesterol level after baseline visit for patients who received pharmaceutical combination therapy of TOFACITINIB and atorvastatin.

Table 2 presents the ACR20 (American College of Rheumatology 20% improvement in response rate) response rates (relative to Enrollment Visit, i.e., pre-TOFACITINIB treatment). At Baseline Visit (after 6 week treatment of TOFACITINIB), two treatment groups have comparable high response rates (76.0% versus 76.6%). The response rates stay high at Week 12 after 6 week treatment of atorvastatin or placebo added-on.

TABLE 2

ACR20* Response Rate

| | TOFACITINIB 10 mg BID | |
|---|---|---|
| | Atorvastatin | Placebo |
| Baseline | | |
| N | 50 | 47 |
| Number (%) of responders | 38 (76.0) | 36 (76.6) |
| Week 12 | | |
| N | 46 | 46 |
| Number (%) of responders | 38 (82.6) | 30 (65.2) |

*Relative to Enrollment Visit.
Source: Table 14.2.28.1

Variations, modifications, and other implementations of what is described herein will occur to those skilled in the art without departing from the spirit and the essential characteristics of the present teachings. Accordingly, the scope of the present teachings is to be defined not by the preceding illustrative description but instead by the following claims, and all changes that come within the meaning and range of equivalency of the claims are intended to be embraced therein.

Each of the printed publications, including but not limited to patents, patent applications, books, technical papers, trade publications and journal articles described or referenced in this specification are herein incorporated by reference in their entirety and for all purposes.

What is claimed is:

1. A method of treating a disease in a mammal, wherein the disease is selected from the group consisting of atherosclerosis, myocardial infarction, hypercholesterolemia, hyperlipidemia, ischemic heart disease, congestive heart failure, acute coronary syndrome, plaque instability, coronary artery disease, cerebrovascular disease, peripheral vascular disease and cardiac risk management, comprising administering to a mammal in need thereof a therapeutically effective amount of a Janus Kinase inhibitor and a HMG-CoA reductase inhibitor or a pharmaceutically acceptable salt thereof or a pharmaceutical composition of pharmaceutical composition comprising:

a Janus Kinase inhibitor or a pharmaceutically acceptable salt thereof; and a HMG-CoA reductase inhibitor or a pharmaceutically acceptable salt thereof; and a pharmaceutically acceptable carrier.

2. The pharmaceutical combination therapy of claim 1, wherein the Janus Kinase inhibitor is a compound of the formula

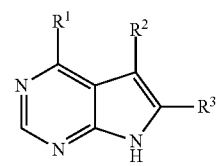

I or the pharmaceutically acceptable salt thereof; wherein $R^1$ is a group of the formula

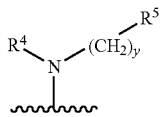

wherein y is 0, 1 or 2;
$R^4$ is selected from the group consisting of hydrogen, ($C_1$-$C_6$)alkyl, ($C_1$-$C_6$)alkylsulfonyl, ($C_2$-$C_6$)alkenyl, ($C_2$-$C_6$)alkynyl wherein the alkyl, alkenyl and alkynyl groups are optionally substituted by deuterium, hydroxy, amino, trifluoromethyl, ($C_1$-$C_4$)alkoxy, ($C_1$-$C_6$)acyloxy, ($C_1$-$C_6$)alkylamino, (($C_1$-$C_6$)alkyl)$_2$amino, cyano, nitro, ($C_2$-$C_6$)alkenyl, ($C_2$-$C_6$)alkynyl or ($C_1$-$C_6$)acylamino; or $R^4$ is ($C_3$-$C_{10}$)cycloalkyl wherein the cycloalkyl group is optionally substituted by deuterium, hydroxy, amino, trifluoromethyl, ($C_1$-$C_6$)acyloxy, ($C_1$-$C_6$)acylamino, ($C_1$-$C_6$)alkylamino, (($C_1$-$C_6$)alkyl)$_2$amino, cyano, cyano($C_1$-$C_6$)alkyl, trifluoromethyl($C_1$-$C_6$)alkyl, nitro, nitro($C_1$-$C_6$)alkyl or ($C_1$-$C_6$)acylamino;
$R^5$ is ($C_2$-$C_9$)heterocycloalkyl wherein the heterocycloalkyl groups must be substituted by one to five carboxy, cyano, amino, deuterium, hydroxy, ($C_1$-$C_6$)alkyl, ($C_1$-$C_6$)alkoxy, halo, ($C_1$-$C_6$)acyl, ($C_1$-$C_6$)alkylamino, amino($C_1$-$C_6$)alkyl, ($C_1$-$C_6$)alkoxy-CO—NH, ($C_1$-$C_6$)alkylamino-CO—, ($C_2$-$C_6$)alkenyl, ($C_2$-$C_6$)alkynyl, ($C_1$-$C_6$)alkylamino, amino($C_1$-$C_6$)alkyl, hydroxy($C_1$-$C_6$)alkyl, ($C_1$-$C_6$)alkoxy($C_1$-$C_6$)alkyl, ($C_1$-$C_6$)acyloxy($C_1$-$C_6$)alkyl, nitro, cyano($C_1$-$C_6$)alkyl, halo($C_1$-$C_6$)alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$)alkoxy($C_1$-$C_6$)acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}N$—CO—O—, $R^{15}R^{16}N$—CO—($C_1$-$C_6$)alkyl, ($C_1$-$C_6$)alkyl-S(O)$_m$, $R^{15}R^{16}NS(O)_m$, $R^{15}R^{16}NS(O)_m$($C_1$-$C_6$)alkyl, $R^{15}S(O)_mR^{16}N$, $R^{15}S(O)_mR^{16}N$($C_1$-$C_6$)alkyl wherein m is 0, 1 or 2 and $R^{15}$ and $R^{16}$ are each independently selected from hydrogen or ($C_1$-$C_6$)alkyl; or a group of the formula

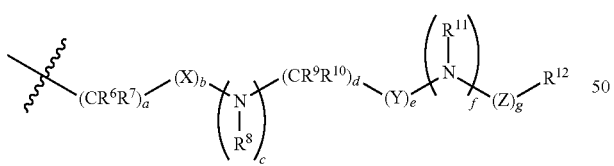

II wherein a is 0, 1, 2, 3 or 4;
b, c, e, f and g are each independently 0 or 1;
d is 0, 1, 2, or 3;
X is S(O)$_n$ wherein n is 0, 1 or 2; oxygen, carbonyl or —C(=N-cyano)-;
Y is S(O)$_n$ wherein n is 0, 1 or 2; or carbonyl; and
Z is carbonyl, C(O)O—, C(O)NR— or S(O)$_n$ wherein n is 0, 1 or 2;
$R^6$, $R^7$, $R^8$, $R^9$, $R^{10}$ and $R^{11}$ are each independently selected from the group consisting of hydrogen or ($C_1$-$C_6$)alkyl optionally substituted by deuterium, hydroxy, amino, trifluoromethyl, ($C_1$-$C_6$)acyloxy, ($C_1$-$C_6$)acylamino, ($C_1$-$C_6$)alkylamino, (($C_1$-$C_6$)alkyl)$_2$amino, cyano, cyano($C_1$-$C_6$)alkyl, trifluoromethyl($C_1$-$C_6$)alkyl, nitro, nitro($C_1$-$C_6$)alkyl or ($C_1$-$C_6$)acylamino;
$R^{12}$ is carboxy, cyano, amino, oxo, deuterium, hydroxy, trifluoromethyl, ($C_1$-$C_6$)alkyl, trifluoromethyl($C_1$-$C_6$)alkyl, ($C_1$-$C_6$)alkoxy, halo, ($C_1$-$C_6$)acyl, ($C_1$-$C_6$)alkylamino, (($C_1$-$C_6$)alkyl)$_2$ amino, amino($C_1$-$C_6$)alkyl, ($C_1$-$C_6$)alkoxy-CO—NH, ($C_1$-$C_6$)alkylamino-CO—, ($C_2$-$C_6$)alkenyl, ($C_2$-$C_6$)alkynyl, ($C_1$-$C_6$)alkylamino, hydroxy($C_1$-$C_6$)alkyl, ($C_1$-$C_6$)alkoxy($C_1$-$C_6$)alkyl, ($C_1$-$C_6$)acyloxy($C_1$-$C_6$)alkyl, nitro, cyano($C_1$-$C_6$)alkyl, halo($C_1$-$C_6$)alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$)alkoxy($C_1$-$C_6$)acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}N$—CO—O—, $R^{15}R^{16}N$—CO—($C_1$-$C_6$)alkyl, $R^{15}C(O)NH$, $R^{15}OC(O)NH$, $R^{15}NHC(O)NH$, ($C_1$-$C_6$)alkyl-S(O)$_m$, ($C_1$-$C_6$)alkyl-S(O)$_m$—($C_1$-$C_6$)alkyl, $R^{15}R^{16}NS(O)_m$, $R^{15}R^{16}NS(O)_m$($C_1$-$C_6$)alkyl, $R^{15}S(O)_mR^{16}N$, $R^{15}S(O)_mR^{16}N$($C_1$-$C_6$)alkyl wherein m is 0, 1 or 2 and $R^{15}$ and $R^{16}$ are each independently selected from hydrogen or ($C_1$-$C_6$)alkyl;
$R^2$ and $R^3$ are each independently selected from the group consisting of hydrogen, deuterium, amino, halo, hydoxy, nitro, carboxy, ($C_2$-$C_6$)alkenyl, ($C_2$-$C_6$)alkynyl, trifluoromethyl, trifluoromethoxy, ($C_1$-$C_6$)alkyl, ($C_1$-$C_6$)alkoxy, ($C_3$-$C_{10}$)cycloalkyl wherein the alkyl, alkoxy or cycloalkyl groups are optionally substituted by one to three groups selected from halo, hydroxy, carboxy, amino($C_1$-$C_6$)alkylthio, ($C_1$-$C_6$)alkylamino, (($C_1$-$C_6$)alkyl)$_2$amino, ($C_5$-$C_9$)heteroaryl, ($C_2$-$C_9$)heterocycloalkyl, ($C_3$-$C_9$)cycloalkyl or ($C_6$-$C_{10}$)aryl; or $R^2$ and $R^3$ are each independently ($C_3$-$C_{10}$)cycloalkyl, ($C_3$-$C_{10}$)cycloalkoxy, ($C_1$-$C_6$)alkylamino, (($C_1$-$C_6$)alkyl)$_2$ amino, ($C_6$-$C_{10}$)arylamino, ($C_1$-$C_6$)alkylthio, ($C_6$-$C_{10}$)arylthio, ($C_1$-$C_6$)alkylsulfinyl, ($C_6$-$C_{10}$)arylsulfinyl, ($C_1$-$C_6$)alkylsulfonyl, ($C_6$-$C_{10}$)arylsulfonyl, ($C_1$-$C_6$)acyl, ($C_1$-$C_6$)alkoxy-CO—NH—, ($C_1$-$C_6$)alkyamino-CO—, ($C_5$-$C_9$)heteroaryl, ($C_2$-$C_9$)heterocycloalkyl or ($C_6$-$C_{10}$)aryl wherein the heteroaryl, heterocycloalkyl and aryl groups are optionally substituted by one to three halo, ($C_1$-$C_6$)alkyl, ($C_1$-$C_6$)alkyl-CO—NH—, ($C_1$-$C_6$)alkoxy-CO—NH—, ($C_1$-$C_6$)alkyl-CO—NH—($C_1$-$C_6$)alkyl, ($C_1$-$C_6$)alkoxy-CO—NH—($C_1$-$C_6$)alkyl, ($C_1$-$C_6$)alkoxy-CO—NH—($C_1$-$C_6$)alkoxy, carboxy, carboxy($C_1$-$C_6$)alkyl, carboxy($C_1$-$C_6$)alkoxy, benzyloxycarbonyl($C_1$-$C_6$)alkoxy, ($C_1$-$C_6$)alkoxycarbonyl($C_1$-$C_6$)alkoxy, ($C_6$-$C_{10}$)aryl, amino, amino($C_1$-$C_6$)alkyl, ($C_1$-$C_6$)alkoxycarbonylamino, ($C_6$-$C_{10}$)aryl($C_1$-$C_6$)alkoxycarbonylamino, ($C_1$-$C_6$)alkylamino, (($C_1$-$C_6$)alkyl)$_2$amino, ($C_1$-$C_6$)alkylamino($C_1$-$C_6$)alkyl, (($C_1$-$C_6$)alkyl)$_2$amino($C_1$-$C_6$)alkyl, hydroxy, ($C_1$-$C_6$)alkoxy, carboxy, carboxy($C_1$-$C_6$)alkyl, ($C_1$-$C_6$)alkoxycarbonyl, ($C_1$-$C_6$)alkoxycarbonyl($C_1$-$C_6$)alkyl, ($C_1$-$C_6$)alkoxy-CO—NH—, ($C_1$-$C_6$)alkyl-CO—NH—, cyano, ($C_5$-$C_9$)heterocycloalkyl, amino-CO—NH—, ($C_1$-$C_6$)alkylamino-CO—NH—, (($C_1$-$C_6$)alkyl)$_2$amino-CO—NH—, ($C_6$-$C_{10}$)arylamino-CO—NH—, ($C_5$-$C_9$)heteroarylamino-CO—NH—, ($C_1$-$C_6$)alkylamino-CO—NH—($C_1$-$C_6$)alkyl, (($C_1$-$C_6$)alkyl)$_2$amino-CO—NH—($C_1$-$C_6$)alkyl, ($C_6$-$C_{10}$)arylamino-CO—NH—($C_1$-$C_6$)alkyl, ($C_5$-$C_9$)heteroarylamino-CO—NH—($C_1$-$C_6$)alkyl, ($C_1$-$C_6$)alkylsulfonyl, ($C_1$-$C_6$)alkylsulfonylamino, ($C_1$-$C_6$)alkylsulfonylamino($C_1$-$C_6$)alkyl, ($C_6$-$C_{10}$)arylsulfonyl, ($C_6$-$C_{10}$)arylsulfonylamino, ($C_6$-$C_{10}$)arylsulfonylamino($C_1$-$C_6$)

alkyl, (C$_1$-C$_6$)alkylsulfonylamino, (C$_1$-C$_6$) alkylsulfonylamino(C$_1$-C$_6$)alkyl, (C$_5$-C$_9$)heteroaryl or (C$_2$-C$_9$)heterocycloalkyl.

3. The method of claim 1, wherein the Janus Kinase inhibitor is selected from the group consisting of:
- Methyl-[4-methyl-1-(propane-1-sulfonyl)-piperidin-3-yl]-(7H-pyrrolo[2,3-d]-pyrimidin-4-yl)-amine;
- 4-Methyl-3-[methyl-(7H-pyrrolo[2,3-d]pyrimidin-4-yl)-amino]-piperidine-1-carboxylic acid methyl ester;
- 3,3,3-Trifluoro-1-{4-methyl-3-[methyl-(7H-pyrrolo[2,3-d]pyrimidin-4-yl)-amino]-piperidin-1-yl}-propan-1-one;
- 4-Methyl-3-[methyl-(7H-pyrrolo[2,3-d]pyrimidin-4-yl)-amino]-piperidine-1-carboxylic acid dimethylamide;
- ({4-Methyl-3-[methyl-(7H-pyrrolo[2,3-d]pyrimidin-4-yl)-amino]-piperidine-1-carbonyl}-amino)-acetic acid ethyl ester;
- 3-{4-Methyl-3-[methyl-(7H-pyrrolo[2,3-d]pyrimidin-4-yl)-amino]-piperidin-1-yl}-3-oxopropionitrile;
- 3,3,3-Trifluoro-1-{4-methyl-3-[methyl-(5-methyl-7H-pyrrolo[2,3-d]pyrimidin-4-yl)-amino]-piperidin-1-yl}-propan-1-one;
- 1-{4-Methyl-3-[methyl-(7H-pyrrolo[2,3-d]pyrimidin-4-yl)-amino]-piperidin-1-yl}-but-3-yn-1-one;
- 1-{3-[(5-Chloro-7H-pyrrolo[2,3-d]pyrimidin-4-yl)-methyl-amino]-4-methyl-piperidin-1-yl}-propan-1-one;
- 1-{3-[(5-Fluoro-7H-pyrrolo[2,3-d]pyrimidin-4-yl)-methyl-amino]-4-methyl-piperidin-1-yl}-propan-1-one;
- N-cyano-4-methyl-3-[methyl-(7H-pyrrolo[2,3-d]pyrimidin-4-yl)-amino]-N'-propylpiperidine-1-carboxamidine;
- N-cyano-4,N',N'-Trimethyl-3-[methyl-(7H-pyrrolo[2,3-d]pyrimidin-4-yl)-amino]-piperidine-1-carboxamidine;
- Methyl-[(3R,4R)-4-methyl-1-(propane-1-sulfonyl)-piperidin-3-yl]-(7H-pyrrolo[2,3-d]pyrimidin-4-yl)-amine;
- (3R,4R)+4-Methyl-3-[methyl-(7H-pyrrolo[2,3-d]pyrimidin-4-yl)-amino]-piperidine-1-carboxylic acid methyl ester;
- 3,3,3-Trifluoro-1-{(3R│4R)-4-methyl-3-[methyl-(7H-pyrrolo[2,3-d]pyrimidin-4-yl)-amino]-piperidin-1-yl}-propan-1-one;
- (3R,4R)-4-Methyl-3-[methyl-(7H-pyrrolo[2,3-d]pyrimidin-4-yl)-amino]-piperidine-1-carboxylic acid dimethylamide;
- {(3R,4R)-4-Methyl-3-[methyl-(7H-pyrrolo[2,3-d]pyrimidin-4-yl)-amino]-piperidine-1-carbonyl}-amino)-acetic acid ethyl ester;
- 3-{(3R,4R)-4-Methyl-3-[methyl-(7H-pyrrolo[2,3-d]pyrimidin-4-yl)-amino]-piperidin-1-yl}-3-oxo-propionitrile;
- 3,3,3-Trifluoro-1-{(3R,4R)-4-methyl-3-[methyl-(5-methyl-7H-pyrrolo[2,3-d]pyrimidin-4-yl)-amino]-piperidin-1-yl}-propan-1-one;
- 1-{(3R,4R)-4-Methyl-3-[methyl-(7H-pyrrolo[2,3-d]pyrimidin-4-yl)-amino]-piperidin-1-yl}-but-3-yn-1-one;
- 1-{(3R,4R)-3-[(5-Chloro-7H-pyrrolo[2,3-d]pyrimidin-4-yl)-methyl-amino]-4-methylpiperidin-1-yl}-propan-1-one;
- 1-{(3R,4R)-3-[(5-Fluoro-7H-pyrrolo[2│3-d]pyrimidin-4-yl)-methyl-amino]-4-methyl-piperidin-1-yl}-propan-1-one;
- (3R,4R)—N—Cyano-4-methyl-3-[methyl-(7H-pyrrolo[2,3-d]pyrimidin-4-yl)-amino]-N'-propylpiperidine-1-carboxamidine; and
- (3R,4R)—N-Cyano-4,N',N'-Trimethyl-3-[methyl-(7H-pyrrolo[2,3-d]pyrimidin-4-yl)-amino]-piperidine-1-carboxamidine, or a pharmaceutically acceptable salt thereof.

4. The method of claim 1, wherein the Janus Kinase inhibitor is 3-{(3R,4R)-4-Methyl-3-[methyl-(7H-pyrrolo[2,3-d]-pyrimidin-4-yl)-amino]-piperidin-1-yl}-3-oxopropionitrile or a pharmaceutically acceptable salt thereof.

5. The method of claim 1, wherein the HMG-CoA reductase inhibitor is a statin.

6. The method of claim 5, wherein the statin is selected from the group consisting of atorvastatin, fluvastatin, lovastatin, pravastatin, simvastatin, cerivastatin, rivastatin, mevastatin, velostatin, compactin, dalvastatin, fluindostatin, rosuvastatin, pitivastatin, and dihydrocompactin.

7. The method of claim 5, wherein the statin is atorvastatin.

8. The method of claim 5, wherein the statin is atorvastatin calcium salt.

9. The method of claim 1, wherein the mammal is a human.

10. The method of claim 1, wherein the Janus Kinase inhibitor or a pharmaceutically acceptable salt thereof and the HMG-CoA reductase inhibitor or a pharmaceutically acceptable salt thereof are administered simultaneously, sequentially or separately.

11. The method of claim 1, wherein the ratio of Janus Kinase inhibitor or a pharmaceutically acceptable salt thereof to the HMG-CoA reductase inhibitor or a pharmaceutically acceptable salt thereof is about 2:1 to about 1:40 w/w.

12. The method of claim 1, wherein the dosage form is selected from the group consisting of a solution, a suspension, a tablet, a pill, a sachet, a capsule, multiparticulates and a powder.

* * * * *